(12) United States Patent
Dickopf et al.

(10) Patent No.: US 7,955,638 B2
(45) Date of Patent: Jun. 7, 2011

(54) SURFACE FOR THE IMMOBILIZATION OF LIGANDS

(75) Inventors: Stefan Dickopf, Heidelberg (DE); Holger Ottleben, Heidelberg (DE); Harald Rau, Dossenheim (DE); Renate Sekul, Ladenburg (DE); Kristina Schmidt, Heidelberg (DE); Dirk Vetter, Heidelberg (DE)

(73) Assignee: Graffinity Pharmaceuticals AG, Heidelberg (DE)

( * ) Notice: Subject to any disclaimer, the term of this patent is extended or adjusted under 35 U.S.C. 154(b) by 588 days.

(21) Appl. No.: 11/980,015

(22) Filed: Oct. 30, 2007

(65) Prior Publication Data

US 2008/0167196 A1   Jul. 10, 2008

Related U.S. Application Data

(62) Division of application No. 10/297,244, filed as application No. PCT/DE01/02072 on Jun. 1, 2001, now abandoned.

(30) Foreign Application Priority Data

Jun. 2, 2000 (DE) .................................. 100 27 397

(51) Int. Cl.
    *G01N 1/31* (2006.01)
(52) U.S. Cl. ..................... 427/2.13; 436/518; 435/287.1; 427/2.11
(58) Field of Classification Search ........................ None
    See application file for complete search history.

(56) References Cited

U.S. PATENT DOCUMENTS

| 5,834,224 A | 11/1998 | Ruger et al. |
| 6,475,808 B1 * | 11/2002 | Wagner et al. .................. 506/18 |
| 2002/0127577 A1 | 9/2002 | Eichler et al. |

FOREIGN PATENT DOCUMENTS

| EP | 0485874 | 5/1992 |
| EP | 0574000 | 12/1993 |
| WO | WO90/05503 | 5/1990 |

OTHER PUBLICATIONS

Himmel et al., Fabrication of a carboxyl-terminated organic surface with self-assembly of functionalized terphenylthiols: the importance of hydrogen bond formation, 1998, J Am Chem Soc, 120: pp. 12069-12074.*

Smith et al., Formation, spectroscopic characterization, and application of sulfhydryl terminated alkanethiol monolayers for the chemical attachment of DNA onto gold surfaces, 2001, Langmuir 17: pp. 2502-2507.*

Derda, et al., Solid-phase synthesis of alkanethiols for the preparation of self-assembled monolayers, 2007, Langmuir, 23(22): 11164-11167.*

"Molecular recognition at self-assembled monolayers: Optimization of surface functionalization", J. Chem. Phys. 99 (9), Nov. 1, 1993 (4 pgs).

* cited by examiner

*Primary Examiner* — N. C. Yang
(74) *Attorney, Agent, or Firm* — Kagan Binder, PLLC

(57) ABSTRACT

The present invention relates to binding surfaces for the immobilization of ligands, ligand surfaces and structured surface arrays which present a plurality of identical or different ligands. The invention further relates to a process for the production and the use of such surfaces and to specific binder molecules which can be used for the preparation thereof.

16 Claims, 6 Drawing Sheets

SURFACE FOR THE IMMOBILIZATION OF LIGANDS

CROSS-REFERENCE TO RELATED APPLICATIONS

This divisional patent application is entitled to and hereby claims the benefit of priority, under 35 U.S.C. §§120 and 121, of the filing date of commonly owned U.S. National Stage patent application Ser. No. 10/297,244, filed Jun. 30, 2003 now abandoned, entitled SURFACE FOR THE IMMOBILIZATION OF LIGANDS; which in turn claims the benefit of priority of the filing date of commonly owned International application PCT/DE01/02072, having a PCT publication number WO 01/92883 A2, filed Jun. 1, 2001, the entire contents of all of which are incorporated herein by reference.

FIELD OF THE INVENTION

The present invention relates to binding surfaces for the immobilization of ligands, ligand surfaces and structured surface arrays which present a plurality of identical or different ligands. The invention further relates to a process for the production and the use of such surfaces and to specific binder molecules which can be used for the preparation thereof.

BACKGROUND

In known processes of interaction analysis, biomolecular interaction is studied with receptor-ligand systems wherein the receptor is usually a biomacromolecule (e.g. a protein or single-stranded DNA) and the ligand is a "probe", a molecule usually of low molecular weight and of biological or synthetic origin (peptides, oligonucleotides or what are referred to as small organic molecules). Such ligands exhibit highly specific structural properties which can interact with a receptor provided it exhibits corresponding structures. The binding to the receptor can take place via one or several ligands. Furthermore, systems are studied wherein both interaction partners are macromolecules (e.g. protein-protein interaction).

Interaction analysis is used in the pharmaceutical and agrochemical industries for researching active substances. The goal is to analyze as large a number of different samples as possible in as short a time period as possible. There is a growing interest to develop testing systems that are able to simultaneously subject a large number of both identical and different molecules to a certain test method for detecting their biospecific binding behavior in order to identify molecules with a specific effect (High-Throughput Screening, HTS). Such a parallelization is closely linked to a simultaneous miniaturization of the testing arrangement and automation of the testing procedure. Furthermore, interaction analysis is used in the research of the genome (polymorphisms (SNP) analysis or expression pattern analysis) and also in food analysis.

It constitutes a practical advantage to bind one of the interaction or binding partners, i.e. the ligand or the receptor, to an organic or inorganic surface, thereby imparting bioactivity to that surface due to the generation of a specific boundary layer. The bond is preferably a covalent bond or a bond formed by adsorption. The immobilization of an interaction partner facilitates the process, such as for example carrying out washing steps, and in combination with a suitable, most of the time optical, detection process (e.g. fluorescence measurement) it may provide information on the presence and degree of interaction between the interaction partners on a molecular level. Comparability and reproducibility of the results are important prerequisites for the interpretation of such data stemming from the interaction between receptor and ligand.

Bioactive surfaces can be generated on different organic and inorganic carriers, such as for example cellulose, silicates or noble metal surfaces. In addition, these carriers can be components of a sensor system. As regards the bioactive boundary layer, films consisting of organic monolayers (Bain and Whitesides, Angew. Chem. 101 [Applied chemistry 101] (1989) 522-8; Zhong and Porter, Anal. Chem. [Analytical chemistry] (1995) 709A-715A) are especially advantageous (physicochemical stability, structural uniformity). Processes are known for preparing such films, wherein for example in a first step alkyl thiols are chemisorbed onto gold. The long-chain molecules assemble on the solid phase as a highly ordered monolayer (self-assembled monolayer, SAM), whereby the gold atoms are complexed by the sulfur functions. Short-chain alkyl thiols however, such as butane thiol, do not form such highly ordered monolayers (R. Berger, et al., Science 27 (1997), 2021-2024). Such SAMs, which in the above-mentioned case do not yet exhibit any specific bioactive structures, are known in the prior art and have been appropriately characterized by means of many physical methods. In Poirier and Pylant, Science, 272 (1996) 1145-8, scanning tunneling microscopic photographs of such monolayers on gold can be found. Apart from gold, other metals as well can serve as the solid phase for such monolayers.

The immobilization of an interaction partner imparting bioactivity to the surface, in particular to a sensor surface, can be effected by so-called anchors. A suitable anchor molecule comprises at least two functional units present at opposite ends of the anchor and allowing binding to the solid phase surface on the one hand and binding to the interaction partner to be immobilized on the other hand. The latter will be referred to in the following as "head group". The nature of the structural element connecting these functional groups should preferably be such that it allows at least the formation of a highly ordered monolayer on the basis of the anchor molecules.

The generation of a bioactive surface using such anchors can be carried out in one or several steps. In the single-step process, the interaction partner is bonded to the head group of the anchor prior to its immobilization. Suitable anchors for the single-step process are described in DE 199 24 606.8. For providing a measuring surface, a complete ligand-anchor conjugate (LAC) is applied onto the surface. This is a molecule connecting the interaction partner to be immobilized and the functional group necessary for binding to the surface by means of a structure capable of forming an SAM.

In multi-step processes, first a binding surface in the form of an organic boundary layer is generated which does not yet exhibit the desired specific structural features, however, which is suitable for binding or can be activated to bind the interaction partners to be immobilized, e.g. ligands. Thus, immobilization of an interaction partner takes place after the generation of a first boundary layer that is not bond-specific by means of a covalent, ionic or complex bond via the head group of the binding component. For this purpose, the head group can be used directly or after it has been activated. Examples of such head groups are described in EP 485 874 A2.

An important advantage of the multi-step process is the fact that the same surface can be used for every interaction partner to be immobilized. Therefore, the resulting concentration of the interaction partners to be immobilized is the same on the surface as well, which is not or not always a given in the single-step process. This is particularly important for the comparability and reproducibility of the different measuring results. However, it also has to be kept in mind that the chemical homogeneity of the non-biospecific binding surface decreases again as the number of potentially necessary activation steps increases.

A step-by-step formation of a diluted binding layer is described in WO 98/40739 A1, wherein in a first step cystamine is applied onto a gold surface and the provision of maleimide as head group is realized in a second chemical reaction. The disadvantage of this process is that another activation step is required for obtaining a binding surface.

Furthermore, reactive amino functions remain that can be responsible for an unspecific binding of macromolecules such as proteins.

It has to be made sure in all multi-step processes that the reaction binding the interaction partner to be immobilized to the anchor via the head group proceeds selectively and in a controlled manner. In this connection, covalent binding of the interaction partner to be immobilized is advantageous since the bioactive surface generated in this manner is chemically more stable, for example with respect to regeneration or storage conditions that can be applied. These advantages particular apply in comparison with the non-covalent binding system streptavidin/biotin which is used frequently.

In particular in the case of immobilization of a small ligand, for instance a so-called "small molecule", the selectivity and the quantitative course of the reaction is of utmost importance for the quantitative evaluation of binding studies or interaction analyses. Here, in contrast to e.g. macromolecular recognition structures, slight differences in the binding strength of the ligand to the receptor often have to be resolved. A ligand of higher affinity offered at a lower density (concentration) than another ligand with a lower binding affinity can lead to an artificially reduced signal, while the other way round a weaker ligand offered at a higher density (concentration) can lead to an artificially increased signal compared to another ligand.

In order to ensure a high degree of selectivity and the possibility of quantitative reactions, reactions with molecules carrying a thiol group or modified by means of a thiol group are employed in biochemistry. The reaction partner is often a macromolecule carrying a maleimidyl group. The product of the reaction of the thiol and the maleimidyl group is a thio succinimide (Michael addition) (G. T. Hermanson, Bioconjugate Techniques, Academic Press 1996, 229-252; Suda et al. Biochem. Biophys. Res. Comm. (1999), 261, 276-282).

A number of reaction partners for the thiol group are known from the prior art (referred to in the following as mercaptophiles), which also allow its selective and quantitative reaction. In addition to maleimides, they include the following compounds:

Iodo- and bromoacetamides, pyridyldithio compounds (G. T. Hermanson, Bioconjugate Techniques, Academic Press 1996, 229-252; C. Boeckler et al., J. Immun. Meth. (1996) 191, 1-10), Michael acceptors in general, acrylic acid derivatives such as the esters, amides, lactones or lactames thereof (K. Matsuura et al. J. Mass Spectrom. (1998) 33, 1199-1208; W. Adam et al. J. Org. Chem. (1995) 60, 578-584), methylene-gem-difluorocyclopropanes (T. Taguchi et al., Tetrahedron (1997). 53, 9497-9508), .alpha.,.beta.-unsaturated aldehydes and ketones (Chen et al., J. Am. Chem. Soc. (1994) 116, 2661-2662) and .alpha.,.beta.-unsaturated sulfones and sulfonamides.

The thiol/mercaptophile system offers the essential advantage that the binding of the interaction partner to be immobilized can be carried out under gentle reaction conditions (ambient temperature, neutral pH, buffer solutions can be used). This is of particular importance when unstable compounds or proteins that denature easily are used. Another advantage is that compared to carboxylic acid, amine or amide groups, a thiol functionality hardly ever occurs in active substances. Thus, an undesired reaction of mercaptophiles that may remain after the immobilization of one interaction partner and the target can largely be avoided.

The thiol/maleimide system is furthermore particularly known for its high degree of selectivity compared to other functionalities such as hydroxyl, amine, carboxyl or hydroxylamine groups. In addition, the formation of the covalent bond is characterized by a high reaction rate (cf. Schelt et al., Bioconj. Chem. (2000), 11, 118-123).

Although such reactions have proven successful in bioconjugate chemistry, anchors comprising both a thiol group for binding to the solid phase surface and a mercaptophilic head group for immobilizing an interaction partner are not disclosed in the prior art since both during synthesis and during the generation of the binding surface both intra- and intermolecular side reactions, and even polymerization, may occur (with respect to the purposeful polymerization of oligothiols with bis-maleimides, cf. L. R. Dix et al., Eur. Polym. J. 31 (1995), 653-658).

EP 485 874 A2 refers to this problem, which is avoided by the exclusive use of disulfide and sulfide groups in the anchor, in order to use for example maleimide as head group for the immobilization of proteins (reaction with —SH group of a Fab' fragment). EP 698 787 A1 as well uses short-chain, maleimide-carrying disulfide anchors for the immobilization of proteins. However, anchors based on disulfide and sulfide groups show the disadvantage that an undesired spatial proximity of the head groups is generated. In this case, the head groups can interfere with each other in the immobilization reaction.

In order to be able to control the spatial proximity of adjacent ligands, EP 485 874 A2 and EP 698 787 A1 do not only apply anchor molecules onto the solid phase surface. Rather, the anchor molecules are "diluted". This is due to the fact that if one partner, for example a ligand is bound to a solid phase carrier for interaction analysis, adjacent ligands on the surface can interfere with each other or with the interaction between the adjacent ligand and the interaction partner to be detected. Whitesides and his colleagues were able to verify this effect in the biospecific adsorption of carbonic anhydrase on benzosulfonamide groups, which were immobilized by means of alkane thiolates on gold, by demonstrating that the degree of undesired irreversible binding of carbonic anhydrase to a mixture of ligand-carrying anchor (immobilized sulfonamide) and diluting component (12,15,18-trioxa-20-hydroxyicosan-1--thiol) decreases as the amount of diluting component in the mixture increases (J. Am. Chem. Soc. 1995, 117, 12009-10).

In order to avoid this disadvantage, mixed surfaces—as shown in FIG. 1—can be applied, which are composed of ligand-carrying anchor molecules and so-called diluting molecules that do not carry any ligands and thus dilute the measuring surface.

The structural nature of the diluting component has to meet the prerequisite that it will not influence the interaction of the immobilized interaction partner and the free interaction partner. In particular, if possible, no specific or unspecific binding between the free interaction partner and the diluting component should occur (e.g. diluent with as high a resistance to protein adsorption as possible). Furthermore, the anchor molecule and the diluting component should be as structurally similar as possible to ensure that their mixing behavior on the solid phase surface is as homogeneous as possible.

On principle, prior art anchors that are based on disulfides and sulfides and thus present two head groups cannot guarantee a stochastic distribution of head-group-carrying molecules and diluting molecules. However, this is necessary in order to ensure a purposeful interaction of the bioactive surface with the free interaction partner later on.

SUMMARY

An immobilization of small ligands (in addition to proteins) in a multi-step process is described by Lahiri et al. in Anal. Chem. 1999, 71, 777-90. 12,15,18-Trioxa-20-hydroxyicosan-1-thiol is used as diluting component. For immobilizing the ligand, the anchor molecule carries a carboxylic acid function as a head group, which in a first step is activated with NHS and then reacted with an amino function in the protein or ligand that was either present or had been introduced. However, this reaction is not complete, and its to yield depends on the degree of dilution on the surface.

Thus, it is the object of the present invention to provide binding surfaces presenting reactive head groups which are capable of entering into selective and highly quantitative reactions with interaction partners to be immobilized. Furthermore, the present invention relates to novel anchor molecules comprising these head groups which can be used, together with diluting molecules, to provide such binding surfaces. The invention further relates to sensor or measuring surfaces obtainable by immobilizing specific interaction partners on the binding surfaces of the present invention, as well as to surface arrays comprising a plurality of such identical or different measuring surfaces.

BRIEF DESCRIPTION OF THE DRAWINGS

The present invention is further illustrated with reference to the accompanying drawings in which.

DETAILED DESCRIPTION

Figure 1:
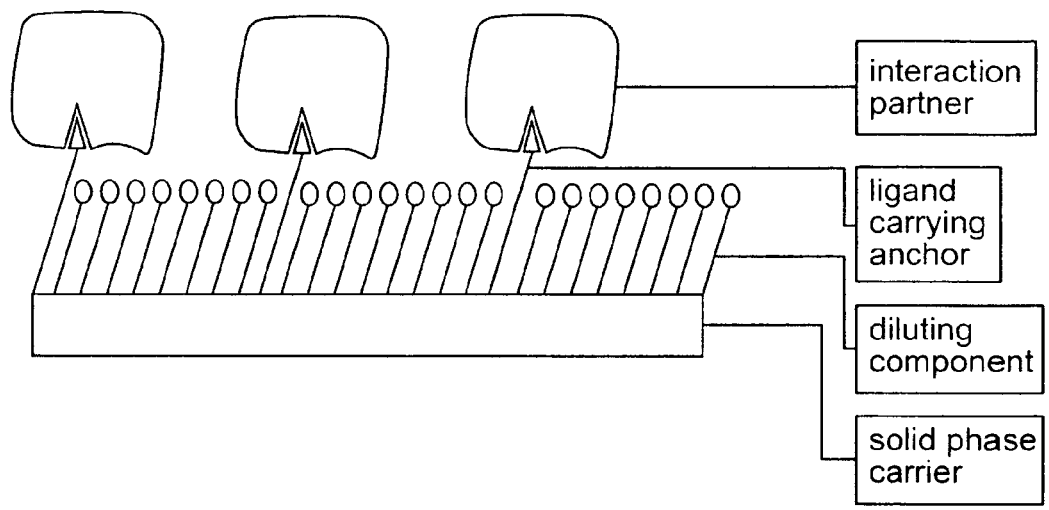
FIG. 1 schematically illustrates the use of mixed surface of a ligand-carrying anchor molecules and diluting molecules that do not carry ligands on a solid phase carrier.

A binding surface according to the present invention comprises a solid phase carrier on which an organic monolayer can assemble spontaneously, preferably comprising at least two components, a binding component and a diluting component (anchor and diluent).

The solid phase carrier consists of a substrate formed by a metal, preferably a noble metal, especially preferred gold, or carries a layer of such a metal. Optionally, the metal layer can be applied with the help of an intermediate layer which serves as a primer. The material used for the substrate depends on measuring method employed. If optical reflection processes such as surface plasmone resonance (SPR) are used, the substrate preferably consists of glass or a plastic material. Due to the use of sulfur-containing compounds for the immobilization of ligands, a gold layer and a chromium layer as a primer are preferably applied onto such substrates.

The spatial design of the solid phase carrier to be used in accordance with the present invention is not restricted, although planar, two-dimensional structures are preferably used for sensor applications. However, depending on the field of application, three-dimensional shapes such as spheres or hollow bodies may be used as well.

Processes for the generation of the binding layers according to the present invention start from a solution of the anchor molecules which is brought into contact with the solid phase carrier. Preferred diluted measuring surfaces are obtained when a solution is used that contains a mixture of anchor molecules and diluting components in a certain molar ratio. Preferably, the solution has a molar ratio of anchor/diluent between 1:2 and 1:10,000. Especially preferred dilution ratios range from 1:10 to 1:100. The total concentration of anchor and diluting components preferably lies in the range of from 0.001 to 100 mmol/l, especially preferred about 0.1 to 1 mmol/l. For generating a homogeneous, large-area binding surface, the entire surface of the solid phase carrier is coated, for example by immersing in a tub, with the (diluted) binding layer. For applying the solution in a spatially defined manner, commercially available pipetting or spotting devices, as well as micropipetting devices or ink-jet processes can be used. Preferably, however, a spatial structure of the measuring surface is achieved by the selective application of the interaction partners to be immobilized onto the large-area binding surface. Suitable solvents include aqueous (e.g. buffer solutions) or organic solvents (e.g. methanol, ethanol, acetonitrile. N,N-dimethylformamide, ethylene glycol) or mixtures thereof.

During the application of the anchors onto the carrier surface, the problems of intramolecular reactions between the anchor molecules described in the prior art can be avoided by working in an acidic medium. For obtaining an acidic environment, the anchor molecule solutions preferably comprise an acid such as trifluoroacetic acid, hydrochloric acid or phosphoric acid.

Anchor molecules suitable for preparing the binding surface according to the present invention comprise at least two functional units present at opposite ends of the anchor. As a group allowing the bonding of the anchor with the surface of a carrier, these anchors comprise a thiol group. For binding the interaction partner to be immobilized to the anchor, the anchor comprises a mercaptophilic head group M as a second functional unit.

The two functionalities are connected via structural element R, which provides for the formation of a self-assembling monolayer on the surface of the carrier. Consequently, the anchors according to the present invention have the following general structure:

Suitable structural elements R that both promote the formation of a monolayer and optionally also allow the adjustment of suitable distances between the head groups and the carrier surface with the help of spacer groups are described with respect to the anchor molecules in the German patent application DE 199 24 606.8, whose entire corresponding disclosure content is hereby incorporated by reference.

Accordingly, the moiety R is a branched or straight-chain, optionally substituted, saturated or unsaturated hydrocarbon chain which may be interrupted by heteroatoms, aromatic and heterocyclic compounds and comprises 5 to 2,000 atoms, including heteroatoms. Preferably, the anchor should comprise structures that impede or prevent a passive adsorption of the free interaction partner both on the anchor structure and the measuring surface. Furthermore, it is advantageous if the anchor comprises a spacer group which allows adjustment of the total chain length and of the flexibility of the LAC. These objects are achieved in a preferred embodiment of the anchor according to the present invention wherein R comprises at least two structural subunits $R^a$ and $R^b$.

However, even if only one of these subunits is present, preferably $R^a$, anchors can be provided that can be used in the present invention to a satisfactory degree.

Preferably, $R^a$ causes the formation of an SAM and for this purpose, it should essentially be hydrophobic. It comprises a branched or straight hydrocarbon chain with 5 to 50 carbon atoms, which may be saturated or partially unsaturated and which may be interrupted by aromatic or heterocyclic groups or heteroatoms. A fully saturated hydrocarbon chain without heteroatoms is preferred. In a preferred embodiment, it has the general formula —$(CH_2)^n$—, wherein n is an integer of 5 to 50, preferably 5 to 25, especially preferred 5 to 18 and most preferred 8 to 12.

Commercially available compounds, in particular functionalized alkanes carrying functional units such as hydroxyl groups, halogen atoms, carboxylic acid groups or mercapto groups at their end groups are suitable for the introduction of $R^a$ in an especially preferred embodiment. These terminal functional units facilitate for example the connection to the adjacent structural units during the synthesis of the anchor. Optionally, they can be used to help introduce necessary components of the anchor, in particular —SH. Examples include 11-mercaptoundecanoic acid and its derivatives.

$R^b$ is preferably a spacer that allows adjustment of the total chain length and of the flexibility of the ligand-anchor conjugate. Preferably, $R^b$ is a hydrocarbon chain which is interrupted by heteroatoms and therefore hydrophilic and impedes a passive adsorption of the receptor. The chain comprises 2 to 1,000 atoms, including heteroatoms; chain lengths of 5 to 500 are preferred, and especially preferred are chain lengths between 10 and 100 atoms.

In a preferred embodiment, $R^b$ is an oligoether of the general formula —$(OAlk)_y$- wherein y is a natural number and Alk represents an alkylene group. A structure wherein y lies between 1 and 100, preferably between 1 and 20 and most preferred between 2 and 10 is preferred. The Alk group preferably comprises 1 to 20, more preferably 2 to 10 and particularly preferred 2 to 5 carbon atoms. Especially preferred is —$OC_2H_4)_y$—.

In a second preferred embodiment, $R^b$ is an oligoamide consisting of dicarboxylic acids and diamines and/or aminocarboxylic acids, wherein the amines independently preferably comprise 1 to 20, more preferably 1 to 10 carbon atoms, and may also be interrupted by further heteroatoms, in particular oxygen atoms. The carboxylic acid monomers independently preferably comprise 1 to 20, more preferably 1 to 10 carbon atoms and may also be interrupted by further heteroatoms, in particular oxygen atoms.

Suitable compounds for the introduction of $R^b$ in an especially preferred embodiment include commercially available compounds such as in particular glycol ethers such as e.g.

triethylene glycol, triethylene glycol monomethylether, tetraethylene glycol, α, ω-diamines such as ethylene-, propylene-, butylene-, or pentylenediamine or 1,8-diamino-3,6-dioxaoctane, but also dicarboxylic acids such as succinic acid, 1,13-diamino-4,7,10-trioxatridecane, 3,6,9-trioxaundecanedioic acid, 8-amino-3,6-dioxaoctanoic acid or 4-aminobenzoic acid as well as their derivatives or combinations of identical components (such as e.g. in the case of 8-amino-3, 6-dioxaoctanoic acid or 4-aminobenzoic acid) or combinations of different components (such as e.g. 1,13-diamino-4, 7,10-trioxatridecane and 3,6,9-trioxaundecanedioic acid in an alternating sequence). An advantage of the use of 4-aminobenzoic acid is the fact that it can easily be detected spectroscopically, for example by means of a UV spectroscopy.

Especially preferred moieties R have the following general formula:

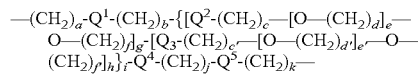

wherein the variables are defined independently of each other as follows and the numeric ranges comprise their respective limiting values as well as the integers contained therein:
$Q^1$, $Q^5$ are —NH—C(O)—, —C(O)—NH— or a bond
$Q^2$, $Q^3$, $Q^4$ are —NH—C(O)— or —C(O)—NH—
a is 5 to 20, preferably 8 to 12, particularly preferred 10;
b is 0 to 5, preferably 0 if $Q^1$ is a bond and 1 to 10, preferably 2 to 7, particularly preferred 3 to 5 in all other cases;
c, c' are 1 to 5, preferably 1 to 3, particularly preferred 1;
d, d' are 1 to 5, preferably 1 to 3, particularly preferred 2;
e, e' are 1 to 5, preferably 1 to 3, particularly preferred 2;
f, f' are 1 to 5, preferably 1 to 3, particularly preferred 1;
g, h are 0 to 3, provided that g+h.gtoreq.1, preferably g+h=2;
i is 1 to 3, preferably 1 to 2, particularly preferred 1;
j is 0 to 5, preferably 1 to 3, particularly preferred 2; and
k is 0 to 5.

Mercaptophilic head groups M are for example iodo- or bromoacetamide, pyridylthio compounds, Michael acceptors in general, acrylic acid derivatives such as its esters, amides, lactones or lactames, methylene-gem-difluorocyclopropanes, α,β-unsaturated aldehydes and ketones as well as α,β-unsaturated sulfones and sulfonamides.

Preferred head groups M are those of the general formula

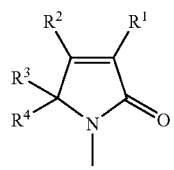

wherein
$R^1$ and $R^2$ are independently hydrogen or $C_1$-$C_5$ alkyl, preferably methyl, ethyl or n-propyl,
$R^3$ and $R^4$ are independently hydrogen or $C_1$-$C_5$ alkyl, preferably methyl, ethyl or n-propyl, or $R^3$ and $R^4$ together form =O and
the binding to the remaining anchor takes place via the nitrogen atom.

Preferably, $R^3$ and $R^4$ together form =O, and most preferred, the head group is a maleimidyl group.

Processes for the synthesis of an anchor molecule can be carried out in a solid phase or in solution. In the case of a preparation in solution, the thiol group is preferably provided with a protective group. Suitable protective groups are described in T. W. Greene, P. G. M. Wuts, Protective Groups in Organic Synthesis, Wiley 1999³, Chapter 6 Protection for the Thiol Group. In a solid phase synthesis, the coupling to the resin preferably takes place via the thiol group so that the thiol group remains masked during synthesis. The cleaving from 25 the solid phase or the protective group is carried out in an acidic environment (for example 1% TFA in dichloromethane). It has been found that this way the side reactions of the thiol and the mercaptophilic compound described in EP 485 874 A2 can be prevented.

The diluting component comprises diluting molecules of the general formula

wherein R is as defined above and X represents a non-mercaptophilic head group. Thus, the diluting component as well includes a preferred moiety R comprising the subunits $R^a$ and $R^b$ and, in a preferred embodiment, corresponding to the structural formula given above.

Ideally, the diluting molecules must not influence the interaction between the immobilized interaction partner and the free interaction partner. In particular, there should be no specific or unspecific binding between the free interaction partner and the diluting molecule. Furthermore, the anchor molecule and the diluting molecule should be as structurally similar as possible in order to ensure that their chemical behavior on the solid phase surface is similar as well (homogeneous miscibility on the solid phase surface). It is advantageous if the total chain length of the diluting molecule is shorter than that of the anchor molecule, for example by one structural unit, such as an ethylene glycol unit. This can for example be achieved by leaving out the last component in the diluent structure when forming the anchor and the diluent from commercially available synthesis components.

In particular, the head group of the diluting molecule should be different from that of the anchor molecule. Preferred head groups for the diluting molecule include methoxy and acylamide groups. Acetamide is especially preferred, in particular if maleimidyl is used as the anchor head group.

A (diluted) measuring surface according to the present invention is generated by a chemical reaction of the interaction partner to be immobilized and the mercaptophilic head group M of the anchor. For this purpose, the interaction partner to be immobilized carries a thiol group which reacts in as selective and quantitative a manner as possible while forming a covalent bond with the head group of the anchor (cf. C. Boeckler et al., J. Immun. Meth. (1996) 191, 1-10). If no suitable functionality is present, it can be generated by converting available functional groups in the interaction partner to be immobilized, e.g. by reductively cleaving a disulfide bond to form a thiol (P. Parham, J. Immunol. 131 (1983), 2895-2902). Furthermore, there is the possibility of providing the interaction partner to be immobilized with an additional molecule, such as for example cysteine, by way of a chemical reaction, which carries the suitable functional group for binding to the head group of the anchor. (With respect to the introduction of a protected 2-aminoethyl thiol in oligonucleotides, see D. Gottschling et al., Bioconjugate Chem. 1998 (9) 831-837.)

The additional molecule can furthermore function as a spacer between the head group of the anchor and the interaction partner to be immobilized, wherein the latter is kept away from the head group and thus the electronic and steric properties of the head group do not affect the binding properties of the interaction partner.

Interaction partners to be immobilized/immobilized interaction partners or ligands in the present invention are chemically unmodified or modified, i.e. provided with a thiol functionality, interaction partners or ligands.

Furthermore, in the context of the present invention, the term immobilized interaction partners generally refers to structural elements which due to their structural characteristics can enter into specific interaction with test substances or subunits thereof. With the help of such immobilized structures, targets can be bound. e.g. in screening processes, which exhibit corresponding compatible structural units. Knowledge of the structure of the ligand then inter alia allows conclusions as to the possible structure or specific structural elements of the receptor.

The term "ligand" is not used consistently in the prior art literature. It should therefore be emphasized that in the present invention the term "ligand" is used in particular for so-called "small molecules" which are preferably bound covalently to the binding surface.

Examples of such ligands include oligomers or small organic molecules, such as peptides, oligonucleotides, carbohydrates (glycosides), isoprenoids or lipid structures. In the relevant literature, the molecular weight is usually the basis for the definition of such small molecules.

The mercaptophilic head group M should preferably serve to immobilize such a ligand, for example a so-called "small molecule" or "low molecular weight molecule".

WO 89/03041 and WO 89/03042 describe molecules with molecular masses of up to 7,000 g/mol as small molecules. Usually, however, molecular masses between 50 and 3,000 g/mol, more frequently between 75 and 2,000 g/mol and most of the time in the range of 100 to 1000 g/mol are mentioned. Reference is made for example to the documents WO 86/02736, WO 97/31269, U.S. Pat. No. 5,928,868, U.S. Pat. No. 5,242,902, U.S. Pat. No. 5,468,651, U.S. Pat. No. 5,547, 853, U.S. Pat. No. 5,616,562, U.S. Pat. No. 5,641,690, U.S. Pat. No. 4,956,303 and U.S. Pat. No. 5,928,643.

In the present invention, the molecular weight of a ligand/ small molecule (without anchor and without additional molecule) should be between 50 and 3,000 g/mol, preferably between 75 and 1,500 g/mol.

Due to their characteristic spatial or electronic structures, caused for example by the functionality of an amino acid, a nucleoside, a heterocyclic compound, an alicyclic compound, an aromatic compound, a terpene, an organophosphorous compound, a chelate complex, a neurotransmitter, a substituted amine, an alcohol, an ester, an ether or a carboxylic acid and its derivatives and combinations thereof, ligands can optionally specifically bind to the receptors. They can be synthesized using reactions known in the prior art (cf. e.g. J. S. Fruchtel, G. Jung, Angew. Chem. Int. Ed. 35, (1996) 17-42). These ligands may have to be chemically modified such that they are able to react with the mercaptophilic head group of the anchors according to the present invention. A list of exemplary compounds that can be bound as ligands, optionally after modification of a functional group or addition of an additional molecule, to the binding surfaces of the present invention can be found in WO 00/73796 A2, which was filed on May 26, 2000 with the German Patent & Trademark Office and whose corresponding disclosure content is hereby incorporated by reference.

However, in addition to ligands, the terms "immobilized interaction partner" or "interaction partner to be immobilized" also encompass macromolecules, preferably biomolecules or receptors such as proteins, oligo- or polypeptides, DNA, RNA, oligo- or polynucleotides, prosthetic groups, vitamins, lipids, mono-, oligo- and polysaccharides, as well as their modifications, and synthetic molecules such as e.g. fusion proteins and synthesized primers. These macromolecules as well may have to be chemically modified for use in the present invention in order to guarantee their covalent binding to the mercaptophilic head group of the anchor molecules.

Molecules acting as free interaction partners are preferably molecules occurring in biological systems or molecules interacting with such molecules, in particular receptors such as proteins, DNA, RNA, oligonucleotides, prosthetic groups, vitamins, lipids, mono-, oligo- and polysaccharides, as well as synthetic molecules such as e.g. fusion proteins and synthesized primers.

For preparing a measuring surface, a solution containing the interaction partner to be immobilized is applied onto the binding surface. It is an advantage of the present invention that the concentration of the ligand (if one is used) on the surface is only determined by the dilution of the binding surface and not by the concentration of the ligand in the solution to be applied. This is in particular advantageous if many interaction partners to be immobilized of which only an approximate concentration is known are processed simultaneously, which is often the case with ligands obtained from combinatorial synthesis. This increases the reproducibility and comparability of different test measurements.

Thus, starting from the binding surface according to the present invention. only one step is required for preparing the biospecific measuring surface, namely contact with the thiol-carrying ligand. For this purpose, the ligand should be present in a slight excess to guarantee a quantitative reaction. Another advantage of the present invention thus lies in the low amount of ligand required for the preparation of a bioactive surface, in particular compared with single-step processes.

The application of the interaction partner to be immobilized is not restricted to specific processes; however, conventional pipetting or spotting devices, but also stamping or ink-jet processes can be employed for a more precise localization of the active areas on the binding surface.

Another aspect of the present invention relates to the provision of an array comprising a plurality of fields on a planar solid phase carrier. Each individual field can be used as a separate measuring surface. Preferably, these measuring surfaces differ in the type of interaction partner immobilized on each one, whereby a single measuring surface can both represent a single type of interaction partner and a mixture of different interaction partners. For this purpose, a variety of interaction partners to be immobilized are applied onto the binding surface and subjected to a measuring process.

The spatial structure of the resulting array can be predetermined by mechanical structuring the carrier. When structured carrier plates are used as sensor surfaces in the present invention, they preferably comprise a plurality of evenly positioned fields with addressable positions for the generation of binding surfaces wherein these fields are located in low-depth cavities. This provides a barrier for the liquid while at the same time the surface is kept as small as possible in order to minimize possible unspecific adsorption phenomena. Furthermore, these fields comprise a layer of the material allowing the binding of the thiol-functionalized anchors. Preferably, the cavities have a depth of 20 to 100 µm and the anchors are immobilized at their bottom which is formed for example by a metal or metal oxide, preferably a noble metal such as gold.

With the help of such fields it is possible to prevent or minimize disadvantages with respect to unspecific binding or spilling over. Furthermore, the manufacture of such a carrier plate can be made inexpensive by the use of processes and materials employed in photo lithography and etching techniques applied in semiconductor technology.

Figure 7:
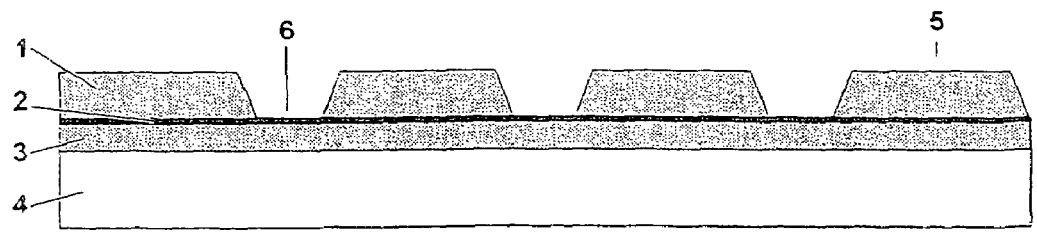
FIGS. 7-9 illustrate schematically cross-sections of alternative embodiments of carrier plates used in the present invention.
Figure 8:
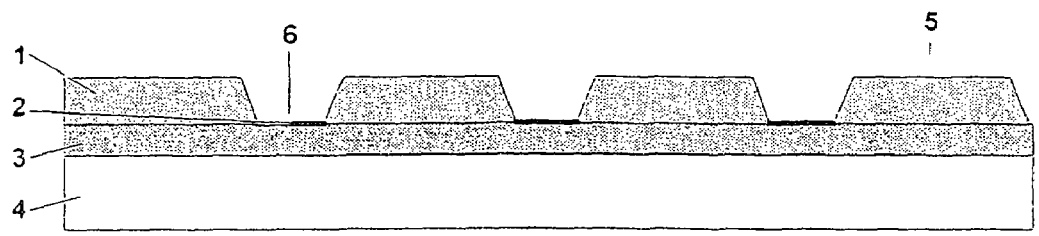
Figure 9:
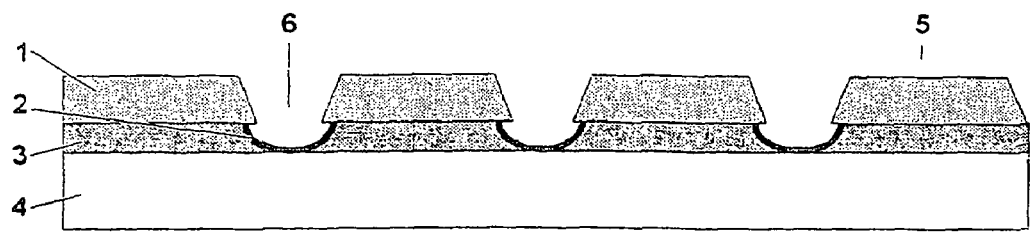

In the following, preferred embodiments of such a carrier plate are described in more detail with reference to the Figures. FIGS. 7 to 9 each show a schematic detail of a cross-section of a preferred carrier plate.

For preparing a carrier plate (5) according to FIG. 7, a copper-clad base material (4) can be used which preferably already carries a metal layer (3) such as copper and which is provided with said carrier layer (2) by means of a galvanic deposition process. The thickness of the carrier layer is only a few micrometers, the exact thickness necessary for generating a closed layer. After electroplating the plate is provided with an UV-exposable protective layer (1). For this purpose, either photoresists common in semiconductor production or other protective paints that are UV-exposable and can therefore be structured can be used. The paint layers preferably have a thickness of 20 µm to 100 µm. In one exposure step, an image of a mask is projected onto the protective layer. The mask preferably exhibits round or rectangular/square patterns. After a developing step, defined openings are formed in the protective layer which expose the carrier layer underneath. Thus, after structuring, the protective layer that can be photostructured also forms the walls of the cavities (6) and thus the form of the cavity (6) and its opening. If application and structuring of the protective layer (1) is carried out prior to the application of the carrier layer (2), a carrier (5) as shown in FIG. 8 is obtained.

FIG. 8 shows a carrier plate (5) with deeper cavities (6) wherein, however, the portion of unprotected wall surface is not increased. This carrier plate preferably has a basis material (4) on whose surface a metallic coating (3) is provided, which in turn is provided with a protective layer (1). At least one cavity (6) is provided in the protective layer (1) and the metal layer (3), which in the area of the metal layer (3) well-shaped and is provided with a carrier layer (2) and which in the area of the protective layer (1) tapers towards the depression, wherein the lower rim of the cavity portion provided in the protective layer (1) has a smaller radius than the upper rim of the cavity portion formed in the metal layer (3).

The production of a carrier plate as shown in FIG. 9 also starts from a coated plate. In that case, however, the thickness of the layer already present (3) is preferably 100 μm to 150 μm. By means of a photoresist (not shown in the Figure), the layer (3) is structured such that it already exhibits wells. Then the plate is coated with the carrier layer (2) by means of a galvanic process. In a second photolithographic step, a protective layer (1) is structured such that a structure is formed in the protective layer (1) above the cavities (6) etched into the layer (3). The depth of the thus formed cavity (6) is the sum of the depth of the etched structure and the thickness of the protective layer (1).

Preferably, the cavities are arranged such that a regular, preferably Cartesian, grid of columns and lines is formed on the carrier plate. The size and shape of the carrier plate can be selected as desired and can easily be adapted to the detection system used. If spotting robots are used for immobilizing the anchors or interaction partners, or if the binding surface is present on microtitration plates, the distance between the fields should preferably be adjusted to the microtitration format or the spotting device used. The number of fields can also exceed the number of subunits of the microtitration plate, i.e. multiple fields can be used per surface. For example, a square carrier plate of about 12.times.12 cm may comprise a total of 9216 fields which can be covered by means of a pipetting robot from six conventional 1536 microtitration plates.

However, a spatially structured presentation of identical or different immobilized to interaction partners can also be achieved by covalently binding the interaction partner to a predetermined portion of the binding surface after an amount of liquid has selectively been applied, without it being necessary to physically divide the surface into individual compartments. For example, techniques for applying reagent spots onto metal or metal oxide surfaces as described in EP-A-0 872 735 can analogously be applied to the binding surfaces of the present invention. If solutions of the interaction partners/ligands are applied onto a homogeneous binding surface, the concentration of the ligand/interaction partner on the finished measuring surface is determined by the dilution of the binding surface. Consequently, there is the additional advantage compared to EP 872 735 A1 that precisely defined amounts of liquid only have to be applied to the solid phase carrier surface once to generate a measuring array (namely when the binding layer is generated).

The present invention can be employed in HTS, in the research of active substances or in medical diagnostics. Suitable measuring methods for detecting interaction between an immobilized (surface-bound) interaction partner/ligand and a free interaction partner/receptor wherein the solid phase carrier only serves for the immobilization of one interaction partner, are based on the verification of the specific binding reaction by means of electrochemical (electro immunoassays), radiochemical (e.g. radioimmunoassay), mass-sensitive or optical processes such as fluorescence or luminescence measurements, in particular enzyme assays. For the latter, the so-called ELISA technique (enzyme-linked immunosorbent assay, immunoassays using solid-phase technique) is preferred.

Reflecto-optical processes such as surface plasmone resonance are suitable for a marker-free detection of the interactions. Here, the solid phase carrier is part of the sensor system.

However, due to the advantages described above, the surfaces of the present invention can also be used in classic processes such as affinity chromatography.

EXAMPLES

Example 1

Synthesis of a Diluting Component a) Immobilization of N—($N^5$-Fmoc-5-aminopentyl)-11-mercaptounde-caneamide on Chlorotrityl Resin

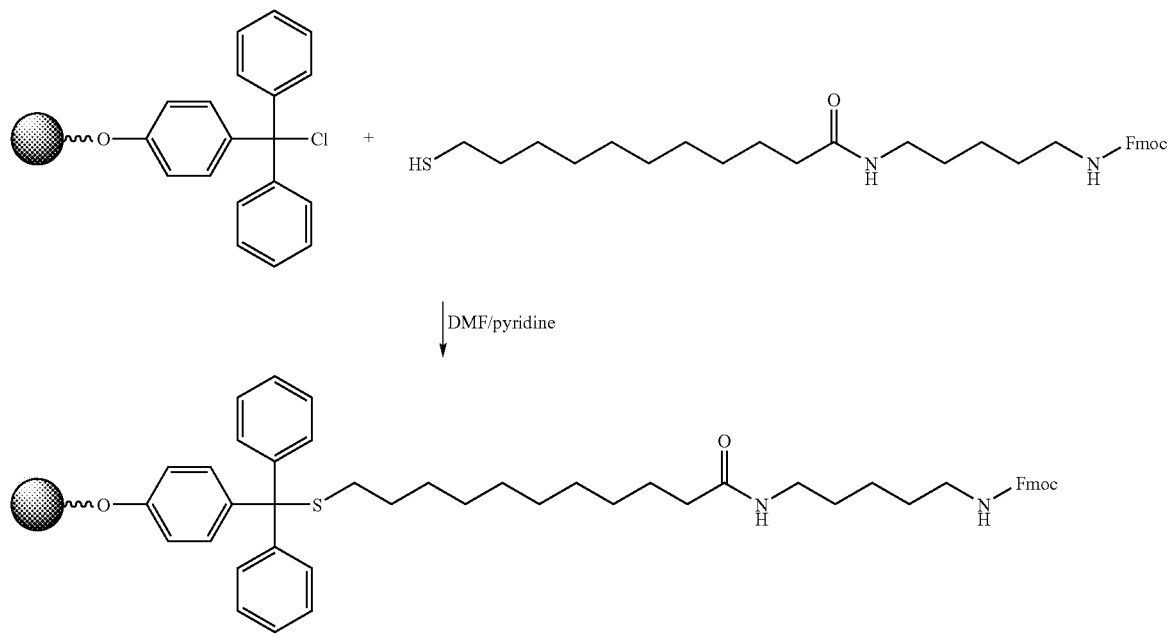

600 mg (1.15 mmol) N—(N$_5$-Fmoc-aminopentyl)-11-mercaptoundecane-amide, obtainable from S-protected 11-mercaptoundecaneamide and Fmoc-1,5-diaminopentane-hydro-chloride, were dissolved in 15 ml DMF and 2 g methoxytrityl-chloride resin (1.6 mmol) (Novabiochem) were added. The suspension was carefully shaken for 1 hour. Then, 500 μl pyridine were added and the suspension was shaken for another 3 hours. Afterwards, the resin was washed once with N,N-dimethylformamide (DMF), once with 5% water in DMF, four times with DMF, three times with dichloromethane and twice with hexane and dried under vacuum. The loading of the resin with N—(N$^5$-Fmoc-5-aminopentyl)-11-mercaptoundecaneamide was determined by means of Fmoc analysis (G. B. Fields, R. L. Noble, Int. J. Peptide Protein Res. 1990, 35, 161-214) to be 0.35 mmol/g (yield: 60% of the theoretical value).

b) General Protocol for Coupling Fmoc-8-amino-3,6-dioxa-octanoic Acid (Fmoc-Ado)

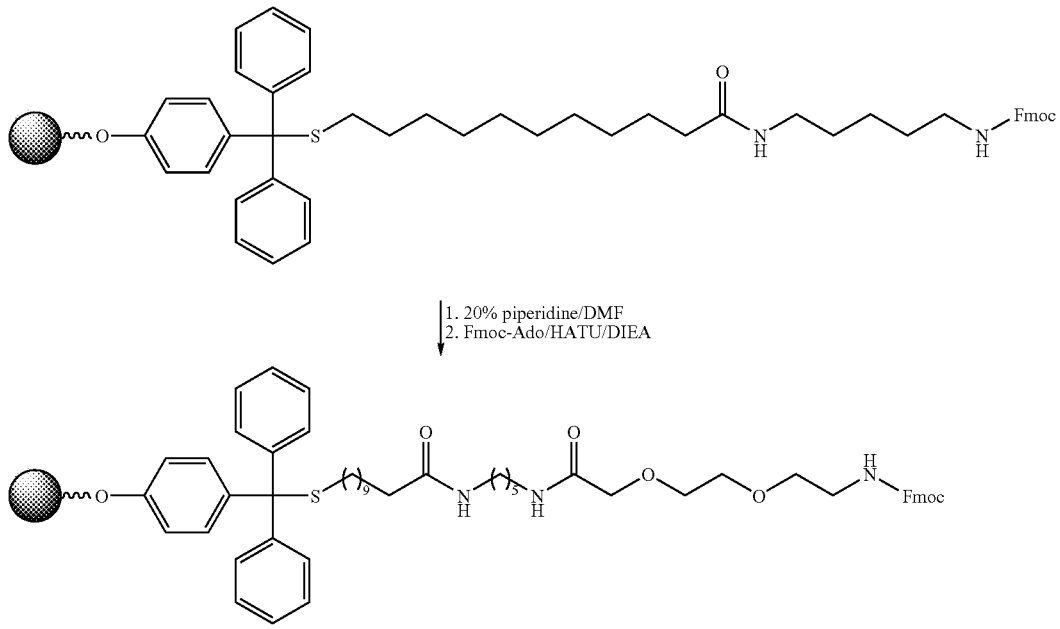

For cleaving off the Fmoc protective group, 1 g of the loaded resin (0.35 mmol) was carefully stirred for 20 min in 15 ml 1/3 (v/v) piperidine/DMF and then washed six times with DMF. The coupling of Fmoc-8-amino-3,6-dioxa-octanoic acid was carried out by incubating the resin for 4 hours with a solution of 270 mg (0.70 mmol) Fmoc-8-amino-3,6-dioxa-octanoic acid. 270 mg (0.71 mmol) O-(7-azabenzotriazole-1-yl)-N,N,N',N'-tetramethyluroniumhexafluorophospha-te (HATU) and 250 μl (1.44 mmol) ethyldiisopropylamine (DIEA) in 7 ml DMF. Then the resin was washed five times with DMF, three times with dichloromethane and twice with hexane and then dried.

c) Synthesis of a Diluting Component

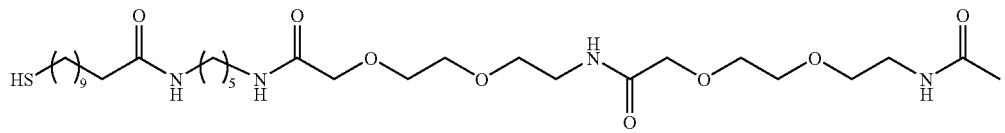

As was described in item b), Fmoc-8-amino-3,6-dioxa-octanoic acid was coupled to 500 mg resin (0.175 mmol) from b) and then the Fmoc protective group was cleaved off as described in b). Subsequently, the free amino groups were acetylated by incubating the resin for 30 min with 10 ml 1/1/2 (v/v/v) acetic acid anhydride/pyridine/DMF. Then the resin was washed five times with DMF and three times with dichloromethane. Cleaving of the product from the resin was carried out with 2/18/1 (v/v/v) trifluoroacetic acid/dichloromethane/triethylsilane. The product was purified by means of preparative RP-HPLC and analyzed by means of LC/MS.

LC-MS (calc.): [M+H]$^+$ 635.5 (635.4), [M+Na]$^+$ 657.5 (657.4)

Example 2

Synthesis of an Anchor Component

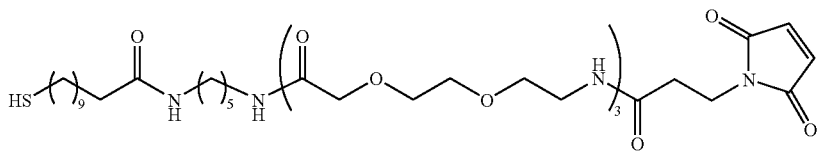

As described in 1b), Fmoc-8-amino-3,6-dioxa-octanoic acid was twice coupled to 100 mg of the resin of 1b) and then the Fmoc protective group was cleaved off. Then 3-maleinimidopropionic acid was coupled by a 1-hour incubation of the resin with 4 eq. 3-maleinimidopropionic acid and 4 eq. diisopropylcarbodiimide in DMF (c=0.15 M).

Then the resin was washed five times with DMF and three times with dichloromethane. Cleaving of the product from the resin was carried out with 2/18/1 (v/v/v) trifluoroacetic acid/dichloromethane/triethylsilane. The product was purified by means of preparative RP-HPLC and analyzed by means of LC/MS.

LC-MS (calc.): $[M+H]^+$ 889.2 (889.5) $[M+Na]^+$ 911.1 (911.5)

Example 3

Preparation of a Binding Surface

The binding surface consists of the anchor component from Example 2 and the diluting component from Example 1.

First of all, stock solutions of the individual components are prepared by dissolving the solids in ethylene glycol/0.1% TFA with the desired molar concentration which is verified by means of Ellman's test (G. L. Ellman, Arch. Biochem. Biophys. 82 (1959), 70-77) or based on the extinction coefficient at 295 nm. Then the stock solutions of anchor and diluting components are mixed in the desired ratio (1:10, v/v) and the gold surface is incubated with this 100 μ.M to 1 mM solution for 1 hour at room temperature. It is then washed with methanol/0.1% TFA and several times with water/acetic acid (2 ppm) and dried in a nitrogen stream.

Example 4

Immobilization of a Ligand ("Small Molecule")

The coupling of Ac-p-Tyr-Cys-$NH_2$, to the binding surface from Example 3 is carried out by incubating a 10-100 μM solution of the compound for 15 to 30 min. Then the surface is rinsed with acetic acid (2 ppm) in water and dried. Subsequently, it is washed with acetic acid (2 ppm) in water and with isopropanol and the surface is dried in a nitrogen stream.

Example 5

Immobilization of Proteins on a Biacore™. J1 Chip

The preparation of the protein surface is carried out by incubating the binding surface from Example 3 (1:10 dilution) with a 17 μM solution of caspase 7T7 (modified by means of a T7 and an oligo-His tag) in 0.2 M $NaH_2PO_4$/$Na_2HPO_4$, pH 7, (20 min, room temperature). Then the chip is washed with acetic acid/water (1 .μl/500 ml), treated for 5 min with 10 mM 2-mercaptoethanol in 0.2 M $NaH_2PO_4$/$Na_2HPO_4$, pH 7, washed with acetic acid/water (see above) and dried in a nitrogen stream.

The success of the protein immobilization is verified by means of SPR on Biacore™ 3000 by spraying on a 6.7 nM solution (HBS, pH 7.4) of an anti-T7 antibody (Novagen) or a 11 nM solution (HBS, pH 7.4) of an anti-oligo-histidine antibody (Sigma).

The change in the SPR signal (in RU) after spraying on 100 μl antibody solution (flow rate: 10 μl/min, run buffer: HBS, pH 7.4) was as follows:

| antibody | RU |
| --- | --- |
| anti-T7 andibody, 6.7 nM | 206 |
| anti-oligo-His antibody, 11 nM | 1067 |

Example 6

Grazing-Angle FTIR

The goal of this measuring method is the vibrational spectroscopy of a thin layer located on a metal surface. The IR light at a grazing incidence is reflected off the metal surface. Measurements are only carried out with IR light polarized in the incidence plane since light with a perpendicular polarization direction cannot contribute to the measurement. Furthermore, only the transition dipole moments which comprise portions at least parallel to the E-field of the radiation contribute to the absorption.

When the molecules located on the surface are oriented, additional selection rules for the appearance of the bands in the spectrum are available. This measuring method is now sensitive enough to measure IR spectra of even monomolecular films, typically resulting in absorption values of some mOD. In the following measurements, a commercially available FTIR device (Bio-Rad FTIR Spectrometer Model FTS 175 C) was used.

Figure 2:
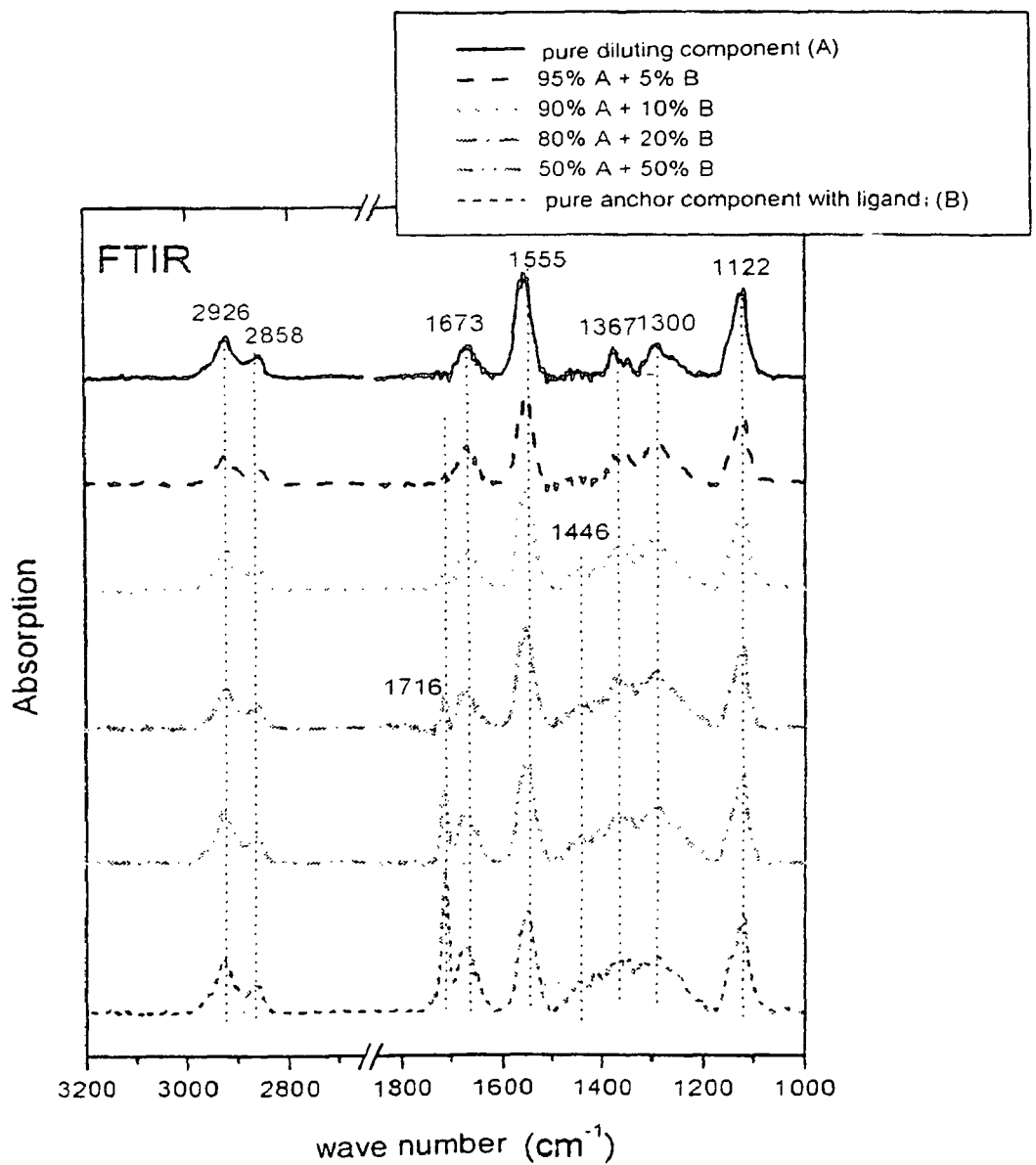
FIG. 2 shows FTIR spectra of various concentrations of diluting component (A) and anchor component with ligand (B).
Figure 3:
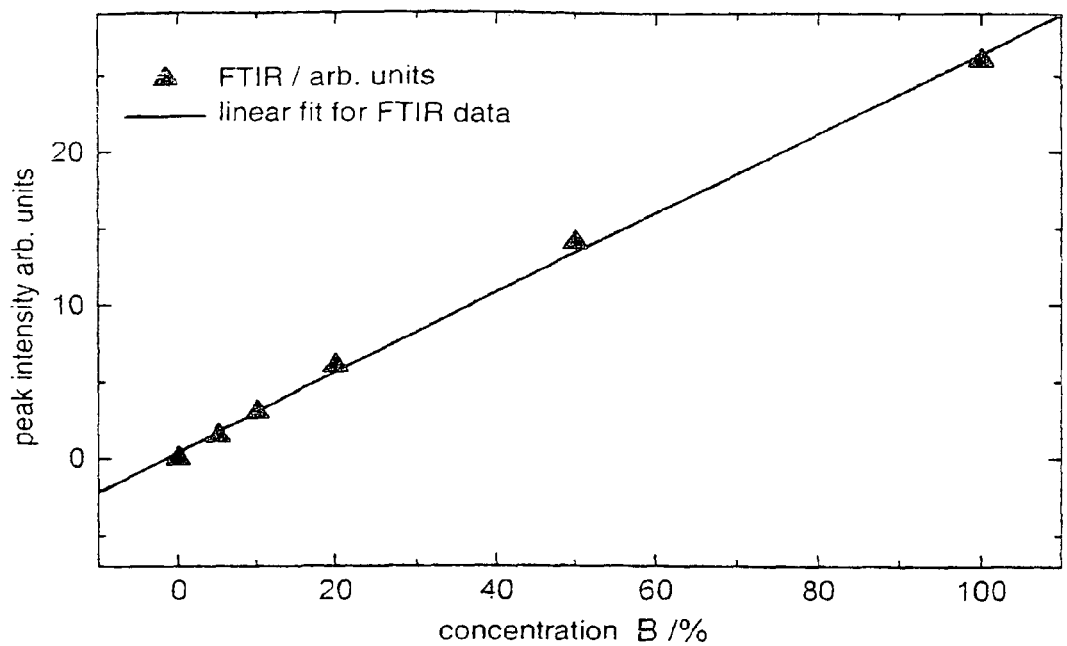
FIG. 3 shows the area of the peak at 1716 cm$^{-1}$ of FIG. 1 plotted against the concentration of the anchor component with ligand (B).

The upper plot in FIG. 2 shows the FTIR spectrum of the pure diluting component (A). The $CH_2$ bands can be seen in the area of 2.900 $cm^{-1}$, the CONH bands in the area of 1.500 to 1.700 $cm^{-1}$ and the C—O—C band at 1.122 $cm^{-1}$. The bottom-most plot shows the spectrum of the pure anchor component with ligand (B). Compared to the spectrum of the diluent, the band at 1.716 $cm^{-1}$ stands out. This band can be assigned to the imide group of the anchor component. When surfaces are prepared with an increasing anchor component concentration (spectra from top to bottom), a systematic increase in the imide band can be observed. For a quantitative evaluation, the area of the peak at 1.716 $cm^{-1}$ was determined and plotted against the concentration of the anchor component (cf FIG. 3). A linear fit to the measuring data clearly shows the connection and thus the conformity of the anchor molecule concentration on the gold surface and the concentration in the solution during gold coating.

Example 7

XPS and Ellipsometry Measurements

In X-ray photoelectron spectroscopy (XPS) the kinetic energy of the electrons formed after the interaction of atoms and mono-energetic X-rays according to the photoelectric effect is verified. As an X-ray source, use was made of $MgK_{\alpha 1,1}$ line (h=1253.6 eV) which was aimed at the surface to be tested at an angle of 45°. The detector measures the number of electrons exiting at 45°, classified according to its energy. In the energy spectrum obtained there are peaks at energy levels that correspond to the difference between the energy of the incident X-rays and the binding energy of the electron in the atom. These binding energies are specific to every atom and it is therefore possible to determine the composition of the molecules on the surface. The peak stemming from the Au4f electrons is particularly large. Since from the point of view of the detector the gold is located behind the molecule layer, the electrons detached from the gold will be re-absorbed by the molecule layer. Therefore, the layer thickness d of the sample can be determined based on the Au4f peak of the sample ($I_{sample}$) and the corresponding peak of a pure gold surface ($I_0$) using the formula $d=\lambda \ln I_0 / \ln (I_{sample})$. In this case $\lambda=37$ Å. is the mean free path of the 1.169.6 eV electrons in the layer.

In ellipsometry, the change in the polarization state of light is measured when it is reflected off the system consisting of molecule layer, gold layer and substrate. According to the Fresnel formulae, there is a reflected and a transmitted light ray at every boundary layer of this system. Since these layers are very thin, multiple reflections occur within the molecule and the gold layers, i.e. the amplitudes of the light rays have to be summed up according to their phases. The result of this summation is a reflection coefficient for the light component polarized in the incidence plane and a second one for the component polarized in a perpendicular direction. These two mathematical expressions comprise the parameters of the layer thicknesses and the (complex) refractive indices of the materials. These two reflection coefficients are determined by means of a spectroscopic ellipsometer (in this case J. A. Woollam Co., Inc. M-44®), also as a function of the wavelength. It is then possible to determine the thickness of the molecule layer from the measured wavelength-dependent reflection coefficients taking into account the refractive index of the molecule layer (here 1.45).

The layer thicknesses obtained from XPS measurements and ellipsometric measurements correspond to the length of the diluting molecule from Example 1. In a stretched configuration, the molecular length of the diluting component is 44 Å. Since the molecules do not protrude at a right angle from the surface but are usually bound at a specific angle, the somewhat shorter measured layer thickness (34 .Å.) indicates that these surfaces are SAiMs. A bond angle of the molecules of about 50° with respect to the surface is therefore conceivable.

Example 8

Unspecific Protein Adsorption Resistance of Different Diluents

The protein adsorption resistance was determined by means of surface plasmone resonance on Biacore™ 3000 with the following proteins:

| | |
|---|---|
| 2 ribonuclease A (bovine): | 0.1 mg/ml |
| lysozyme (chicken): | 0.1 mg/ml |
| egg albumin (chicken): | 0.1 mg/ml |
| D-amino-acid oxidase (procine): | 0.1 mg/ml |
| pyruvate kinase (rabbit): | 0.1 mg/ml |
| fibriogen (human): | 1 mg/ml |
| glutathione reductase (wheat germ): | 1 mg/ml |

For the determination of the protein adsorption resistance, all proteins were dissolved in HBS pH 7.4 at the concentrations given above, and 100 µl of each were sprayed to Biacore™ 3000 (flow rate: 20 µl/min, run buffer: HBS pH 7.4) to the corresponding surfaces and the change in the SPR signal (Response Units=RU) was measured. An increase of 1,000 RU corresponds to an amount of protein of 1 $ng/mm^2$.

Figure 4:
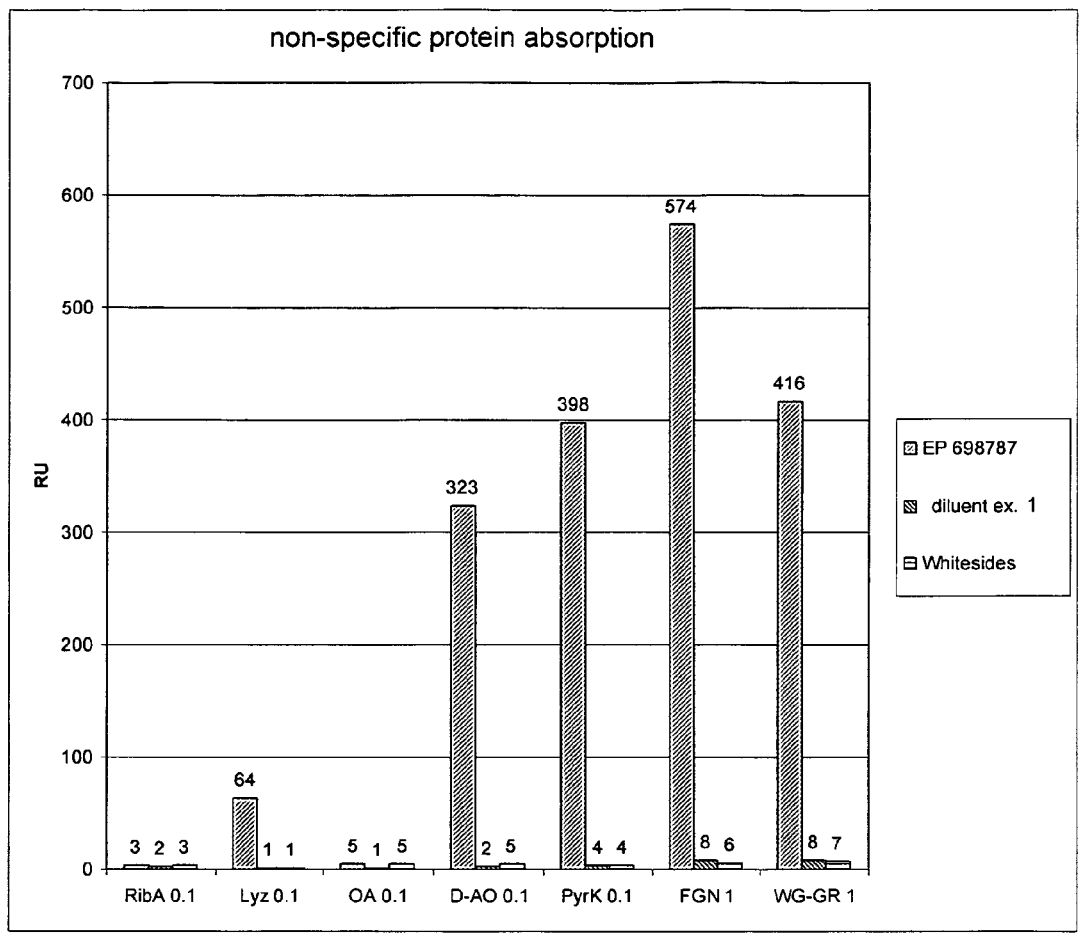
FIG. 4 shows the non-specific protein absorption values for various diluents.

The values shown in FIG. 4 are average values from 4 measurements.

A short-chain disulfide (compound A of EP 698 787), the diluting molecule from Example 1 and 12,15,18-trioxa-20-hydroxyicosan-1-thiol (Whitesides et al. J. Am. Chem. Soc. 1995, 117, 12009-10) were used as a diluents. As can be seen from the results, the chain length of the molecule influences the unspecific adsorption resistance, which increasingly occurs in short-chain diluting molecules.

Example 9

Quantitative Reaction of Phosphotyrosine (pY) at the Binding Surface

Analogously to Example 4, pY with cysteine as additional molecule is used to bind pY to the binding surface from Example 3 ("pY tag").

A gold chip was incubated with a 1:10 mixture of the anchor component from Example 2 and the diluting component from Example 1 in ethylene glycol and 1% TFA at a total concentration of 0.5 mM. Then the chip was washed several times in methanol/0.1% TFA and then in water pH 7.0. Chips pretreated in this manner were dried in a nitrogen stream.

For determining in which concentration range a complete reaction of the presented maleimide functionalities takes place and thus a constant signal intensity of the luminescence can be observed, 0.15 µl of pY tag were applied in dilutions of 10 µM, 1 µM, 100 nM and 10 nM. Four measurements were carried out for each concentration. In the free areas, the maleimide groups were then saturated by incubating the chip in 0.2 M phosphate buffer pH 7.0, 10 mM mercaptoethanol for 30 min.

Such chips were then incubated overnight in BSA blocking solution (50 mM Tris/HCl, 150 mM NaCl, 5 g/l BSA, 0.05% (v/v) Tween-20™, pH 7.3). The verification of the pY groups on the surface of the chip was carried out by means of an immunoassay wherein the chip was first incubated with a 1:5,000 a-pY antibody in blocking solution and then with 1:5,000 anti-mouse-Fab-POD. Between the incubation steps, the blocking solution was washed (2.times.1 min). Prior to the detection of the luminescence signal with the Super-Signal-Plus Substrate from Roche Diagnostics, it was again washed in TBS buffer. The luminescence reaction was observed in a Lumi-Imager (Roche Diagnostics).

Figure 5:
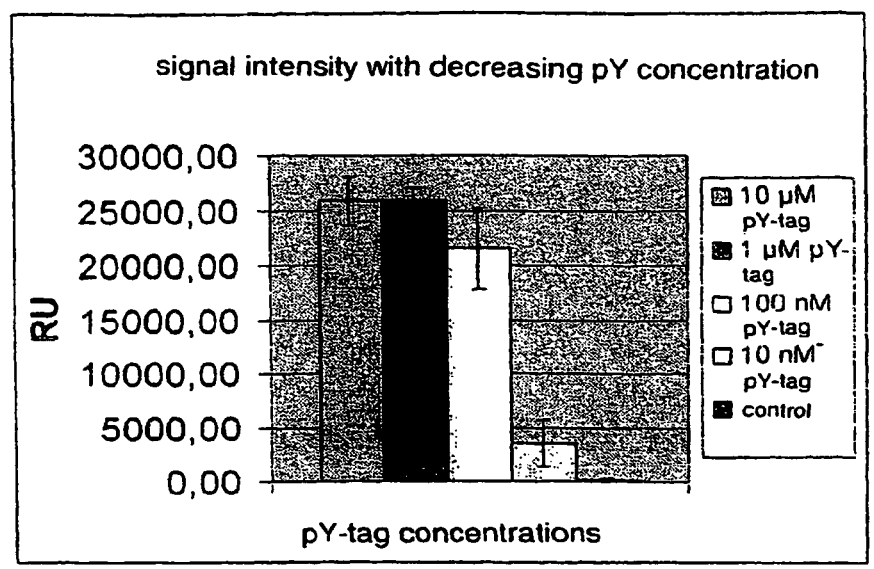
FIG. 5 shows signal intensity with decreasing Phosphotyrosine (pY) concentrations.

Afterwards, the signal intensities were integrated and are shown in the Figure. The standard deviations of the four measurements were calculated and can be inferred from FIG. 5 as error bars.

The results show that the signal intensities are constant throughout a concentration range of three powers of ten within the limit of error. A decrease in the signal can only be observed when the pY tag is highly diluted. The consistency of the signal results from the fact that the reaction of the maleimide with the thiol is approximately quantitative as long as the thiol is present in a certain excess.

Example 10

Preparation of an Array with a Plurality of Measuring Surfaces

A 12×12 cm gold chip (40 nm gold/1 nm chromium on glass) was incubated with a 1:10 mixture (dilution) of anchor component from Example 2 and diluting component from Example 1 in ethylene glycol and 1% trifluoroacetic acid (TFA) at a total concentration of 1.0 mM. Then the chip was washed several times in methanol/1% TFA and then in water pH 7.0. Chips pretreated in this manner were dried in a nitrogen stream.

Subsequently, a library of 9216 thiol-containing ligands were deposited on these chips by means of a spotting device in an arrangement of 96.times.96 spots with a distance of 1.125 mm between the spots. The thiol-containing ligands applied onto the surface are dissolved in a 40 μM solution of 0.2 M Pi, 5 mM EDTA and 10% (v/v) ethylene glycol pH 7.0. The spotting device releases about 10 nl per spot so that in each spot a high excess of the thiol-containing ligand compared to the surface-bound maleimide group is guaranteed and a complete reaction of the maleimide groups can be achieved. In the free areas, the maleimide groups were then saturated by incubating the chip in 0.2 M phosphate buffer pH 7.0, 10 mM mercaptoethanol for 30 min.

Such chips were then incubated overnight in BSA blocking solution (50 mM Tris/HCl, 150 mM NaCl, 5 g/l BSA, 0.05% (v/v) Tween-20®, pH 7.3). The analysis of potential binding partners of the target protein thrombin was carried out by means of an immunoassay.

Figure 6:
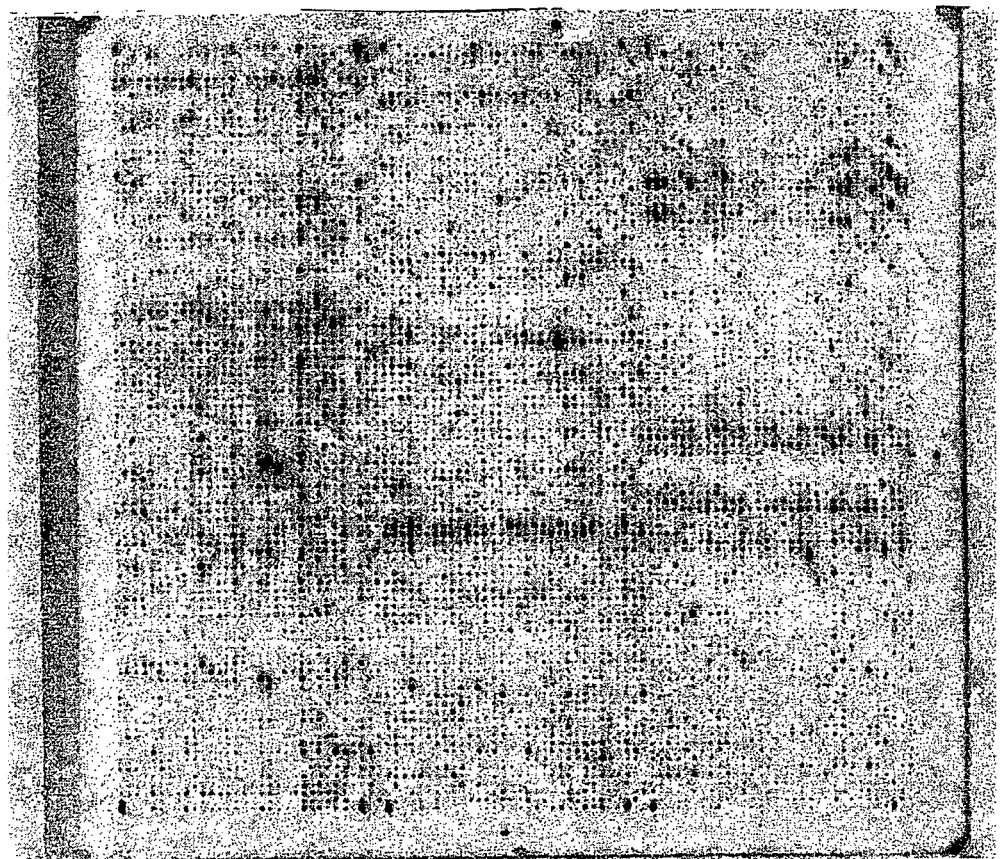
FIG. 6 shows a photograph of the chemical luminescence reaction (10 nM thrombin).

First of all, the chip was incubated for 4 hours in 10 nM thrombin in blocking solution. After washing twice for two minutes in blocking solution, a 1:1,000 dilution of a polyclonal anti-thrombin antibody was incubated with the chip for 2 hours. After again washing twice in blocking solution, an anti-rabbit antibody POD conjugate was incubated with the chip for 2 hours in order to determine the binding activity. Finally, the chip was washed twice for 2 min in TBST. The chemical luminescence reaction was verified by reacting the Lumi-Light Plus Substrate in the Lumi Imager (Roche Diagnostics, Germany). FIG. 6 shows a photograph of the chemical luminescence reaction (10 nM thrombin). Black spots (represented in the Imager as light spots) indicate binding of the thrombin. Discrete intensities can be seen as spots in certain positions. Since every compound on the array has certain spatial coordinates, specific chemical structures can be assigned to the spots.

Example 11

Synthesis of Further Anchor and Diluting Components

1) Structure of Further Anchor and Diluting Compounds (Components) Based on the Reaction of 4-methoxytrityl-Protected Mercaptoundecanoic Acid with Different Diamines.
Reaction Mixtures:
1 g (2.04 mmol) S-(4-methoxytrityl)-mercaptoundecanoic acid
462 mg (2.24 mmol) dicyclohexylcarbodiimide (DCC)
236 mg (2.04 mmol) n-hydroxysuccinimide (NHS)
a) 755.3 mg (850.6 μl; 10.2 mmol) 1,3-diaminopropane
b) 1.51 g (1.49 ml; 10.2 mmol) 1,8-diamino-3,6-dioxaoctane
c) 1.04 g (1.19 ml; 10.2 mmol) 1,5-diaminopentane

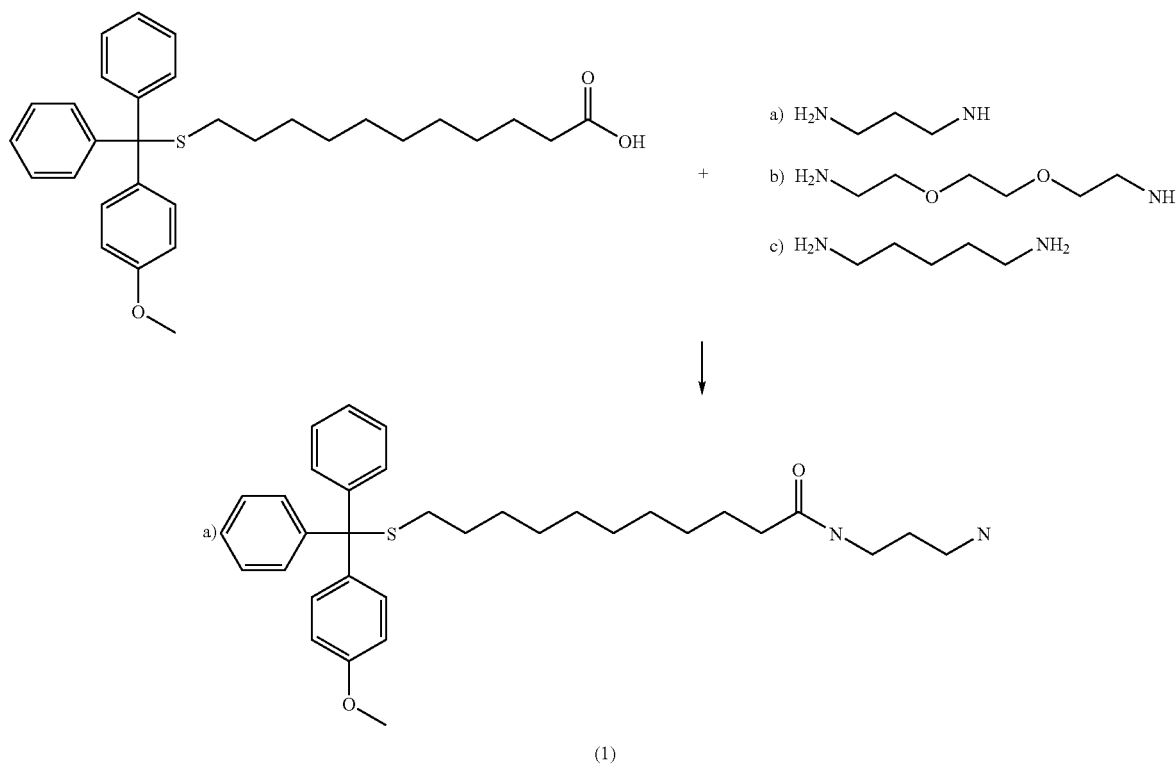

(1)

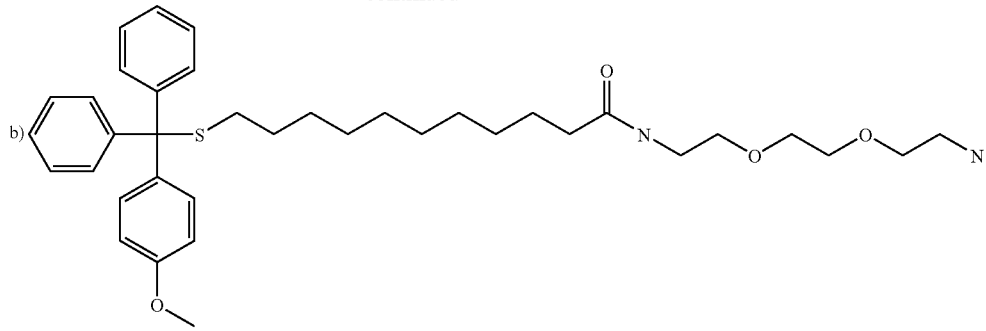

(2)

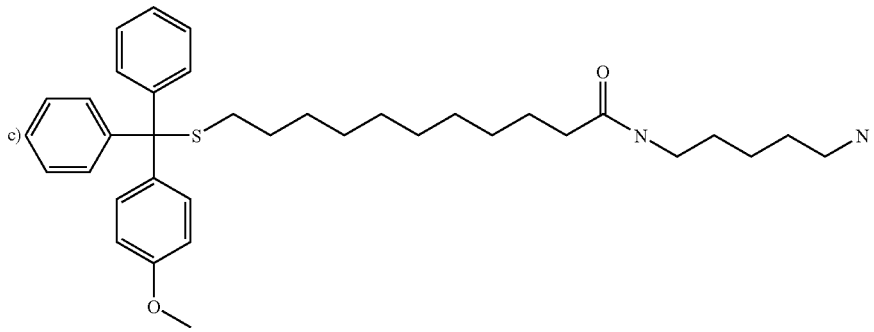

(3)

Preparation:

1 g S-(4-methoxytrityl)-mercaptoundecanoic acid, 462 mg (2.24 mmol) DCC and 236 mg (2.04 mmol) NHS were each dissolved in 20 ml dichloromethane (DCM) and stirred at room temperature for 30 min. The three diamines a) to c) were each dissolved in 20 ml DCM and the S-(4-methoxytrityl)-mercaptoundecanoic acid NHS-ester was added in 10 portions over a time period of 30 min to the diamine solutions under stirring. The reaction mixtures were stirred for 3 hours, the urea was filtered off and the solvent was evacuated in a vacuum. The products were dissolved in ethyl acetate and were each washed three times with 10% sodium carbonate solution, twice with a saturated sodium chloride solution and twice with distilled water. The solutions were dried over sodium sulfate and concentrated in a rotary evaporator until dry.

2) Extension of the Amines (1) to (3) with Trioxaundecanoic Acid.

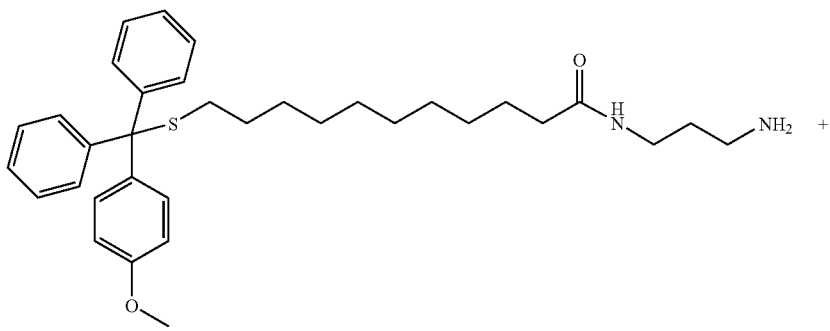

(1)

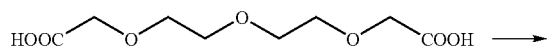

-continued
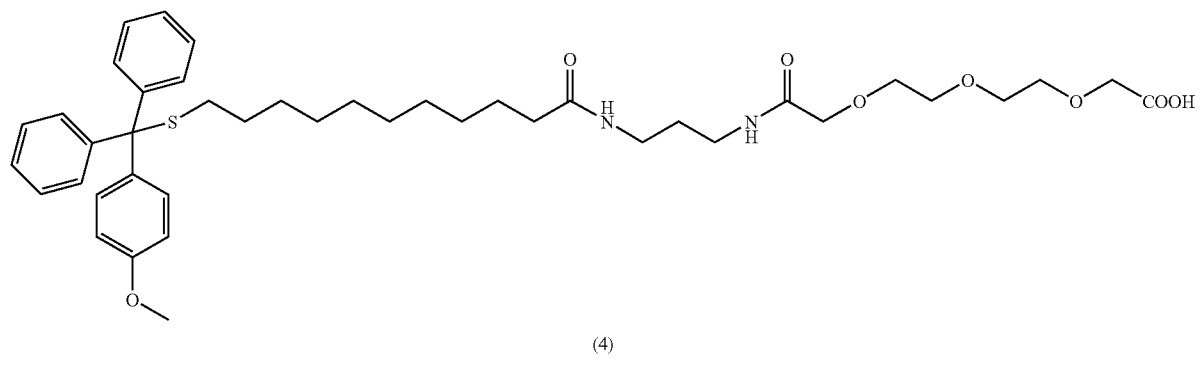
(4)
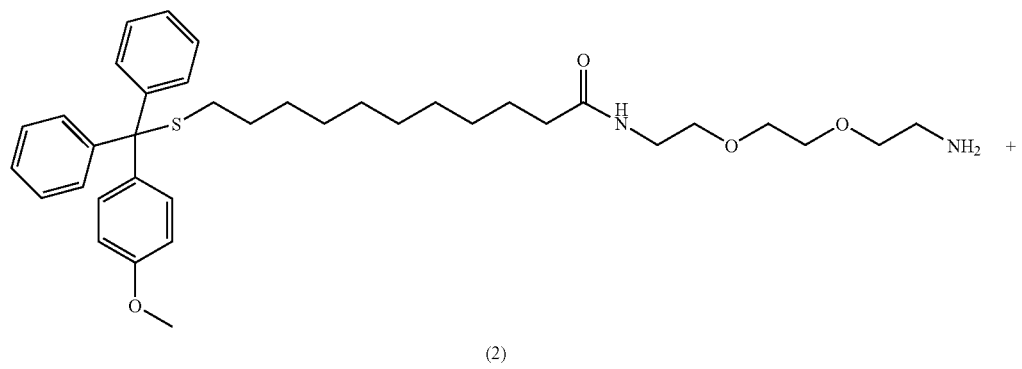
(2)
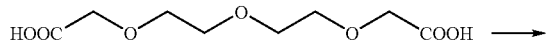
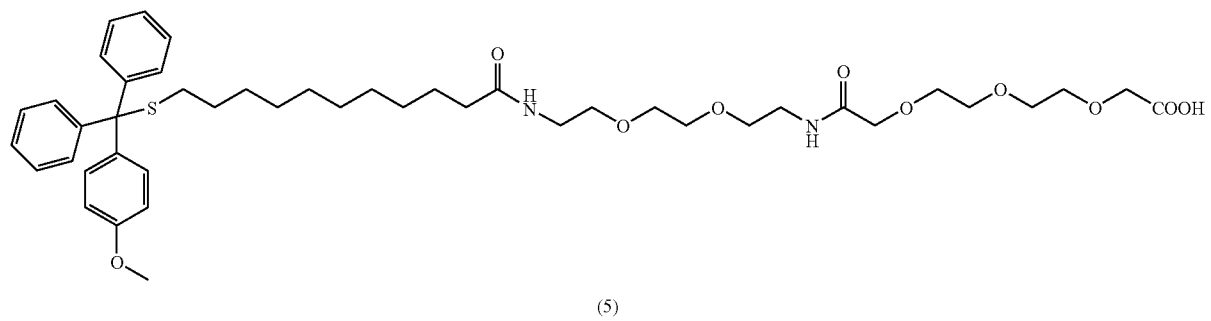
(5)
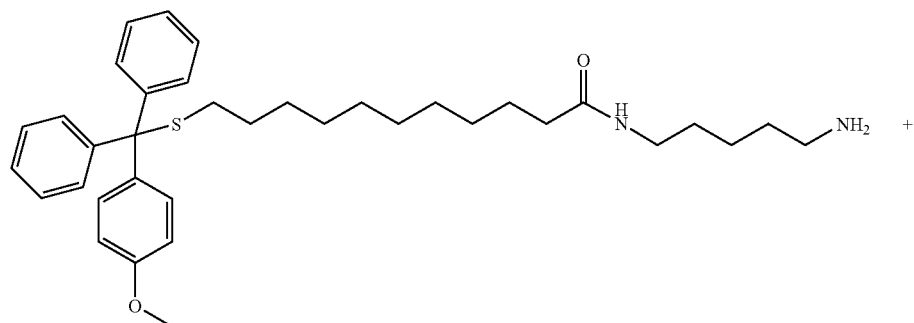
(3)
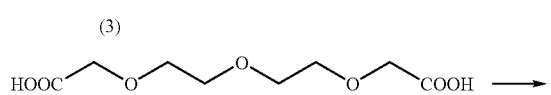

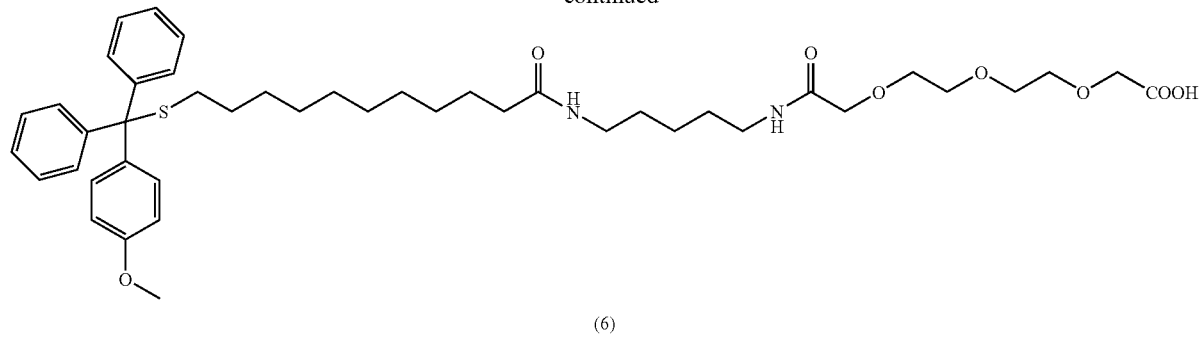

(6)

Reaction Mixtures:
1.27 g (5.71 mmol) 3,6,9-trioxaundecanedioic acid
431.6 mg (2.09 mmol) DCC
220.2 mg (1.90 mmol) NHS
1.23 g (1.62 ml) diisopropylethylamine (DIEA)
a) 1.04 g (1) (1.90 mmol)
b) 1.17 g (2) (1.90 mmol)
c) 1.09 g (3) (1.90 mmol)

Preparation for a) to c):

1.27 g (5.71 mmol) 3,6,9-trioxaundecanedioic acid, 431.6 mg (2.09 mmol) DCC, 220.2 mg (1.90 mmol) NHS and 1.23 g (1.62 ml) diisopropylethylamine (DIEA) were each dissolved in 30 ml DCM and stirred at room temperature for 30 min. Then, 1.90 mmol of amines (1) (1.04 g), (2) (1.17 g) and (3) (1.09 g) were each dissolved in 20 ml DCM and added in 10 portions over a time period of 30 min to the three reaction mixtures under stirring. The mixtures were stirred for 3 hours at room temperature, then the urea was filtered off and the solvent was concentrated until dry. The products (4), (5) and (6) were dissolved in ethyl acetate and were each washed three times with 0.1 M HCl, twice with a saturated sodium chloride solution and twice with distilled water. The solutions were then dried over sodium sulfate and concentrated until dry.

Preparation of the Anchor (13) and the Corresponding Diluents (7) and (8)

Reaction Mixtures:
0.72 g (0.873 mmol) (5)
198 mg (0.96 mmol) DCC
101.8 mg (0.873 mmol) NHS
a) 5 ml 26% aqueous ammonia
b) 266.5 mg (263.4 µL) (4.36 mmol) 2-aminoethanol

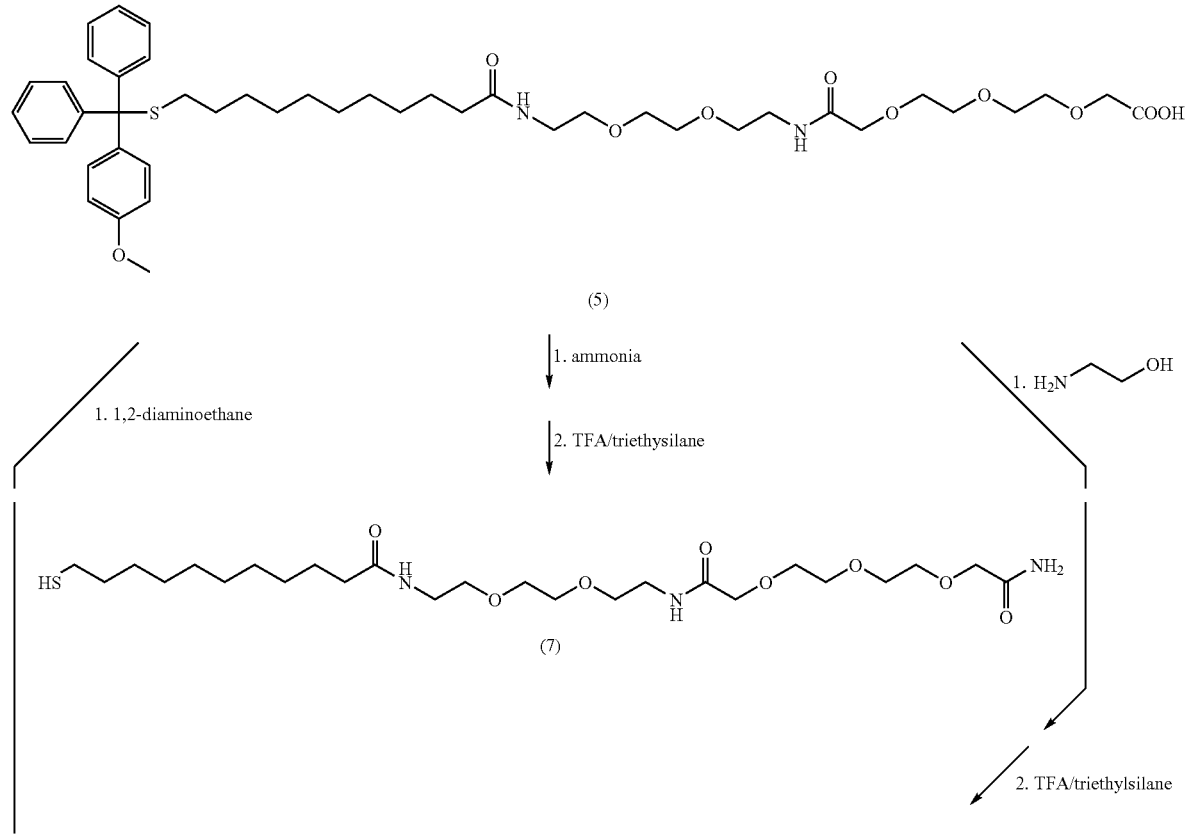

-continued

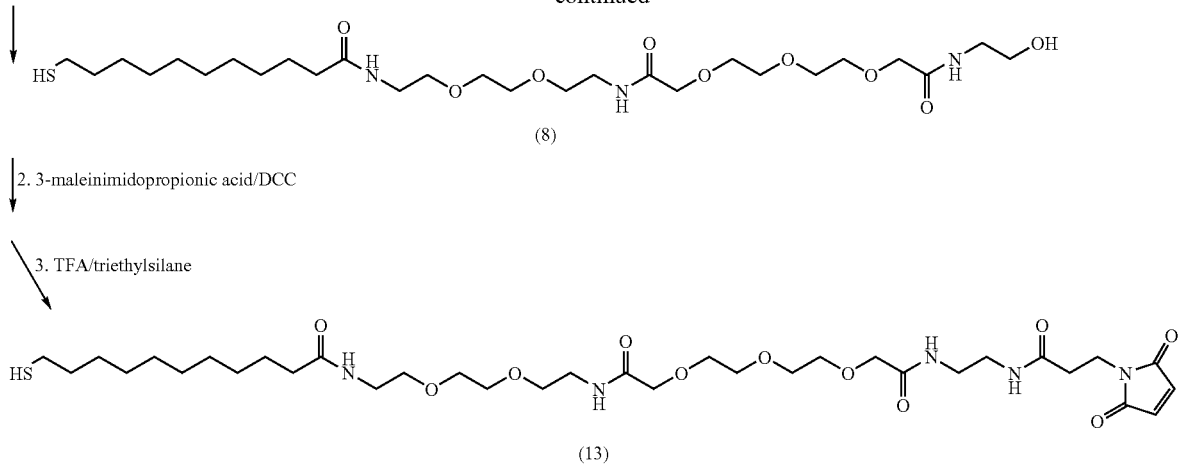

Preparation:

0.72 g (0.873 mmol) (5), 198 mg (0.96 mmol) DCC and 101.8 mg (0.873 mmol) NHS were each dissolved in 30 ml DCM and then stirred for 30 min at room temperature. Then a) 5 ml 29% aqueous ammonia and b) 266.5 mg (263.4 µL) (4.36 mmol) 2-aminoethanol were added under vigorous stirring, and stirring was continued for another 2 hours. Then the urea was filtered off and the solvent was concentrated until dry. The products (7) and (8) were dissolved in ethyl acetate (EE) and were each washed three times with 10% sodium carbonate solution, twice with a saturated sodium chloride solution and twice with distilled water. The solutions were dried over sodium sulfate and concentrated until dry.

For cleaving off the 4-methoxytrityl protective group, compounds (7) and (8) were each dissolved in 20 ml trifluoroacetic acid, 2 ml triethylsilane was added and the mixture was stirred at room temperature for 30 min. The solutions were concentrated until dry and the products were purified by means of preparative HPLC and analyzed by means of LC/MS.

LC/MS (calc.):

[M+H]$^+$ 552.3 (552.7), [M+Na]$^+$ 574.3 (574.7)

[M+H]$^+$ 596.3 (596.8), [M+Na]$^+$ 618.3 (618.8)

200 mg of (5) were reacted with 1,2-diaminoethane analogously to 1a. Then 3-maleinimidopropionic acid was added as described in 4 and the 4-methoxytrityl protective group was cleaved off. The product (13) was purified by means of preparative HPLC and analyzed by means of LC/MS.

LC/MS (calc.): [M+H]$^+$ 746.6 (746.9), [M+Na]$^+$ 748.5 (748.9)

3) Preparation of the Anchors (11) and (12) and the Accompanying Diluents (9) and (10) Formulation:

a) 0.73 g (6) (0.94 mmol)

b) 0.45 g (4) (0.94 mmol)

213.3 mg (1.034 mmol) DCC 108.9 mg (0.940 mmol) NHS 417.9 mg (411.8 µl; 2.82 mmol) 1,8-diamino-3,6-dioxaoctane

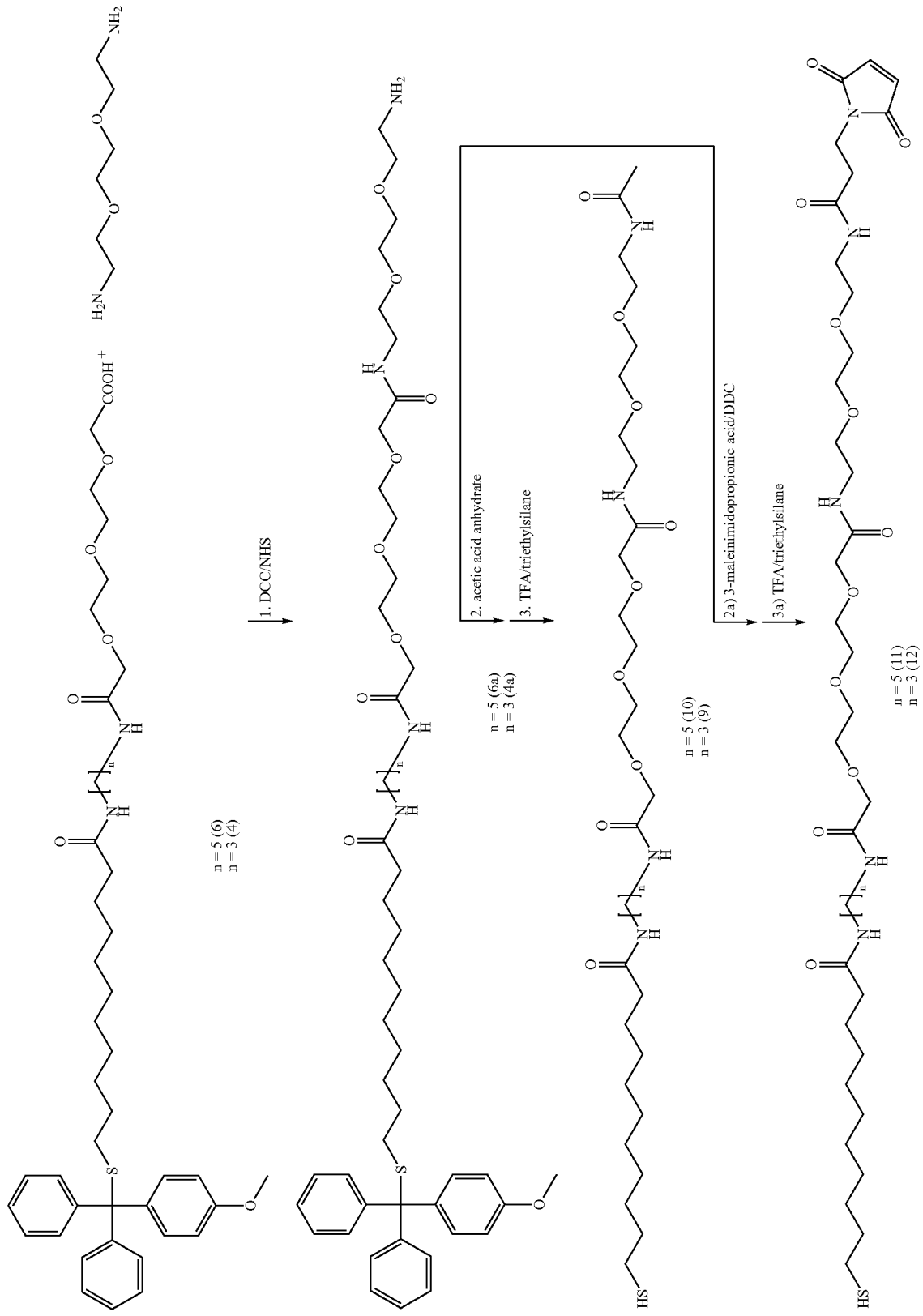

Preparation:

0.73 g (0.94 mmol) (6) and 0.45 g (0.94 mmol) (4) were each dissolved in 20 ml DCM and 213.3 mg (1.034 mmol) DCC and 108.9 mg (0.940 mmol) NHS were added to each solution, which were stirred at room temperature for 30 min. Then 418 mg (412 µl; 2.82 mmol) 1,8-diamino-3,6-dioxaoctane were dissolved in two batches of 20 ml DCM and added to the two reaction mixtures under vigorous stirring. After 3 hours of stirring at room temperature, the urea was filtered off and the solvent was concentrated. The products were dissolved in ethyl acetate and were each washed three times with 10% sodium carbonate solution, twice with a saturated sodium chloride solution and twice with distilled water. The solutions were dried over sodium sulfate and again concentrated until dry.

500 mg each of (4a) and (6a) were dissolved in 20 ml tetrahydrofuran. 2 ml acetic acid anhydride and 2 ml pyridine were added to each solution, which were stirred for 30 min. Then the solvent was concentrated, the products were taken up in ethyl acetate and washed three times with 0.1 M HCl, twice with a saturated NaCl solution and twice with distilled to water. The solutions were dried over sodium sulfate and concentrated until dry.

For cleaving off the 4-methoxytrityl protective group, the products were each dissolved in 20 ml TFA and 2 ml triethylsilane and the mixture was stirred at room temperature for 30 min and then concentrated until dry. The resulting compounds (9) and (10) were purified by means of preparative HPLC and analyzed by means of LC/MS.

LC/MS (calc.):

[M+H]$^+$ 651.5 (651.9), [M+Na]$^+$ 673.5 (673.9)

[M+H]$^+$ 679.6 (679.9), [M+Na]$^+$ 701.6 (701.9)

200 mg each of (4a) and (6a) (0.22 mmol) were dissolved in 10 ml DCM and to each was added a solution of 43 mg (0.25 mmol) 3-maleinimidopropionic acid and 52 mg (0.25 mmol) DCC in 5 ml DCM, and stirred at room temperature for 3 hours. Then the urea was filtered off the solutions were concentrated until dry, and for cleaving off the protective group the products were each dissolved in 10 ml TFA with 2 ml triethylsilane.

After 30 min stirring at room temperature, the solutions were concentrated until dry; the products (11) and (12) were purified by means of preparative HPLC and analyzed by means of LC/MS.

LC/MS (calc.):

[M+H]$_+$ 788.6 (788.9), [M+Na]$^+$ 810.5 (810.9)

[M+H]$^+$ 760.5 (760.9), [M+Na]$^+$ 782.3 (782.9)

The invention claimed is:

1. A process for the generation of a binding layer on the metal surface of a solid phase carrier, comprising the step of contacting a solution of a plurality of identical or different anchor molecules represented by the formula

HS—R-M wherein the structural moiety R provides for the formation of a self-assembling monolayer on the surface and M represents a mercaptophilic head group, with the surface under acidic conditions.

2. The process according to claim 1, wherein a plurality of identical or different diluting molecules represented by the general formula

HS—R—X wherein R is defined as in claim 1 and X represents a non-mercaptophilic head group, is contacted with the surface together with the anchor molecules.

3. The process according to claim 2, wherein the ratio of anchor molecules to diluting molecules ranges from 1:2 to 1:10,000.

4. The process according to claim 2, wherein a planar, non-structured carrier plate or a physically structured carrier plate having a plurality of separate fields for binding the anchors and diluents is used as the solid phase carrier.

5. The process according to claim 1, further comprising the step of covalently binding a plurality of identical or different interaction partners to the mercaptophilic head group of the anchor molecules to form a binding layer having an immobilized interaction partner.

6. The process according to claim 5, wherein the interaction partner is selected from proteins, oligo- or polypeptides, DNA, RNA, oligo- or polynucleotides, prosthetic groups, vitamins, lipids, mono-, oligo- and polysaccharides, as well as their modifications, and synthetic molecules such as e.g. fusion proteins and synthesized primers.

7. The process according to claim 5, wherein the interaction partner is selected from proteins, peptides, oligonucleotides, carbohydrates, isoprenoids, enzymes, lipid structures, saccharides, antibodies, peptide hormones, cytokines, antibiotics and small organic molecules, the small organic molecules being characterized by having a molecular weight ranging from 50 to 3,000 g/mol.

8. The process according to claim 5, wherein the solid phase carrier is divided into separate fields that differ from each other at least in the structure of the bound interaction partners.

9. The process according to claim 1, further comprising the step of applying solutions of interaction partners onto defined, spatially limited areas of the binding layer to form individual measuring surfaces that differ from each other at least in the structure of the bound interaction partners.

10. The process according to claim 9, wherein the solution of the interaction partners is applied by means of a pipetting device, a spotting device, a micropipetting device or an ink-jet process.

11. The process according to claim 1, wherein R comprises a hydrophobic structural moiety $R^a$, formed by a branched or straight-chain hydrocarbon chain of 5 to 50 carbon atoms, which may be saturated or partial unsaturated.

12. The process according to claim 1, wherein R comprises a branched or non-branched hydrophilic spacer $R^b$, formed by hydrocarbon chain of 5 to 1,000 carbon atoms which is interrupted by heteroatoms.

13. The process according to claim 1, wherein R has the following general formula

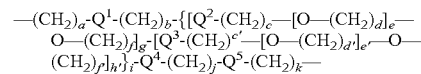

wherein the variables are defined independently of each other as follows and the numeric ranges comprise their respective limiting values as well as the integers contained therein:

$Q^1$, $Q^5$ are —NH—C(O)—, —C(O)—NH— or a bond $Q^2$, $Q^3$, $Q^4$ are —NH—C—(O)— or —C(O)—NH— a is 5 to 20, preferably 8 to 12, particularly preferred 10;

b is 0 to, preferably 0 if $Q^1$ is a bond and 1 to 10, preferably 2 to 7, particularly preferred 3 to 5 in all other cases;

c,c' are 1 to 5, preferably 1 to 3, particularly preferred 1;

d,d' are 1 to 5, preferably 1 to 3, particularly preferred 2;

e,e' are 1 to 5, preferably 1 to 3, particularly preferred 2;

f,f' are 1 to 5, preferably 1 to 3, particularly preferred 1;

g,h are 0 to 3, provided that g+h≧1, preferably g+h=2;

i is 1 to 3, preferably 1 to 2, particularly preferred 1;

j is 0 to 5, preferably 1 to 3, particularly preferred 2; and k is 0 to 5.

14. The process according to claim 1, wherein M is selected from iodo- or bromoacetamide, pyridylthio compounds, Michael acceptors, acrylic acid, (meth)acrylic acid esters, -amides, -lactones, -lactames, methylene-gemdifluorocyclopropanes, α,β-unsaturated aldehydes and ketones and α,β-unsaturated sulfones and sulfonamides.

15. The process according to claim 1, wherein M has the following structure

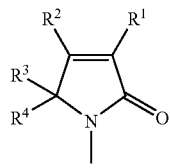

wherein
$R^1$ and $R^2$ are independently hydrogen or $C_1$-$C_5$ alkyl,
$R^3$ and $R^4$ are independently hydrogen or $C_1$-$C_5$ alkyl or
$R^3$ and $R^4$ together form =O.

16. A process for the solid phase synthesis of an anchor molecule having the formula

HS—R-M wherein the structural moiety R provides for the formation of a self-assembling monolayer on the surface and M represents a mercaptophilic head group, comprising the steps of
coupling an anchor molecule precursor comprising a thiol functionality and the structural moiety R to a solid synthesis phase via the thiol group;
reacting the coupled anchor molecule precursor with a compound comprising a mercaptophilic head group to form a molecule of the formula HS—R-M that is coupled to a solid synthesis phase via the thiol group; and
applying an acidic medium to cleave off the anchor molecule from the solid synthesis phase.

* * * * *